(12) United States Patent
Wang et al.

(10) Patent No.: US 11,753,477 B2
(45) Date of Patent: Sep. 12, 2023

(54) PREPARATION AND USE OF ANTI-MET-AND-RON BISPECIFIC ANTIBODY AND ANTIBODY-DRUG CONJUGATE THEREOF

(71) Applicant: PCM TARGETECH, LLC, Amarillo, TX (US)

(72) Inventors: Ming-Hai Wang, Plano, TX (US); Hang-Ping Yao, Amarillo, TX (US)

(73) Assignee: PCM TARGETECH, LLC, Amarillo, TX (US)

( * ) Notice: Subject to any disclaimer, the term of this patent is extended or adjusted under 35 U.S.C. 154(b) by 220 days.

(21) Appl. No.: 17/172,334

(22) Filed: Feb. 10, 2021

(65) Prior Publication Data

US 2021/0395371 A1   Dec. 23, 2021

(30) Foreign Application Priority Data

Jun. 18, 2020   (CN) .......................... 202010562324.X

(51) Int. Cl.
| | |
|---|---|
| *C07K 16/28* | (2006.01) |
| *A61K 47/68* | (2017.01) |
| *A61K 39/00* | (2006.01) |
| *A61K 39/395* | (2006.01) |

(52) U.S. Cl.
CPC .... *C07K 16/2863* (2013.01); *A61K 39/00111* (2018.08); *A61K 39/39533* (2013.01); *A61K 47/6801* (2017.08); *A61K 47/6879* (2017.08); *C07K 16/2866* (2013.01); *A61K 2039/505* (2013.01); *C07K 2317/31* (2013.01); *C07K 2317/515* (2013.01); *C07K 2317/522* (2013.01); *C07K 2317/565* (2013.01); *C07K 2317/60* (2013.01); *C07K 2317/73* (2013.01)

(58) Field of Classification Search
CPC ............ C07K 16/2863; C07K 16/2866; C07K 2317/31; C07K 2317/515; C07K 2317/522; C07K 2317/60; C07K 2317/73; A61K 47/6879; A61K 47/6801; A61K 39/00111; A61K 39/39533; A61K 2039/505
See application file for complete search history.

(56) References Cited

U.S. PATENT DOCUMENTS 11,208,494 B2 *  12/2021  Wang ................. C07K 16/2896

OTHER PUBLICATIONS

Wang, "Potential therapeutics specific to c-MET/RON receptor tyrosine kinases for molecular targeting in cancer therapy," 2010, Acta Pharmacologica Sinica, 31: pp. 1181-1188.*
Shatz, "Knobs-into-holes antibody production in mammalian cell lines reveals that asymmetric afucosylation is sufficient for full antibody dependent cellular cytotoxicity," Aug. 29, 2013, Landes Bioscience, mAbs, 5:6: pp. 872-881.*
G. Köhler et al., Continuous Cultures of Fused Cells Secreting Antibody of Predefined Specificity, Nature, Aug. 7, 1975, pp. 495-497, vol. 256.
A Study to Evaluate the Safety and Pharmacokinetics ABBV-399 in Japanese Participants With Solid Tumors, https://www.clinicaltrials.gov/ct2/show/NCT03311477?term=ABBV-399&draw=2&rank=1, Oct. 17, 2017.
TR1801-ADC in Patients With Tumors That Express c-Met, https://www.clinicaltrials.gov/ct2/show/NCT03859752?term=TR1801-ADC&draw=2&rank=1, Mar. 1, 2019.
A Study of SHR-A1403 in Patients With Advanced Solid Tumor, https://www.clinicaltrials.gov/ct2/show/NCT03856541?term=SHR-A1403&draw=2&rank=1, Feb. 27, 2019.

\* cited by examiner

*Primary Examiner* — Jeffrey Stucker
*Assistant Examiner* — Selam Berhane

(57) ABSTRACT

Provided herein are a preparation method and use of an anti-MET-and-RON bispecific antibody and an antibody-drug conjugate thereof. The anti-MET-and-RON bispecific antibody includes an anti-MET antibody fragment and an anti-RON antibody fragment which are linked to each other through a specific chemical "knobs-into-holes" structure.

11 Claims, 9 Drawing Sheets

Specification includes a Sequence Listing.

SEQUENCE LISTING

```
<160> NUMBER OF SEQ ID NOS: 42

<210> SEQ ID NO 1
<211> LENGTH: 15
<212> TYPE: DNA
<213> ORGANISM: Artificial Sequence
<220> FEATURE:
<223> OTHER INFORMATION: Synthetic

<400> SEQUENCE: 1
aactttggta tacac                                                        15

<210> SEQ ID NO 2
```

```
<211> LENGTH: 48
<212> TYPE: DNA
<213> ORGANISM: Artificial Sequence
<220> FEATURE:
<223> OTHER INFORMATION: Synthetic

<400> SEQUENCE: 2
gtgatatggg gtgatggaat cacaacctat aattcagttc tcaaatcc          48

<210> SEQ ID NO 3
<211> LENGTH: 27
<212> TYPE: DNA
<213> ORGANISM: Artificial Sequence
<220> FEATURE:
<223> OTHER INFORMATION: Synthetic

<400> SEQUENCE: 3
tcttattttt tgggagctat ggtctac                                 27

<210> SEQ ID NO 4
<211> LENGTH: 33
<212> TYPE: DNA
<213> ORGANISM: Artificial Sequence
<220> FEATURE:
<223> OTHER INFORMATION: Synthetic

<400> SEQUENCE: 4
aaggccagtc agagtgtggg tactgctgta gcc                          33

<210> SEQ ID NO 5
<211> LENGTH: 21
<212> TYPE: DNA
<213> ORGANISM: Artificial Sequence
<220> FEATURE:
<223> OTHER INFORMATION: Synthetic

<400> SEQUENCE: 5
tcggcatcca cccggtacac t                                       21

<210> SEQ ID NO 6
<211> LENGTH: 24
<212> TYPE: DNA
<213> ORGANISM: Artificial Sequence
<220> FEATURE:
<223> OTHER INFORMATION: Synthetic

<400> SEQUENCE: 6
caacaatata gcacttctcg gacg                                    24

<210> SEQ ID NO 7
<211> LENGTH: 5
<212> TYPE: PRT
<213> ORGANISM: Artificial Sequence
<220> FEATURE:
<223> OTHER INFORMATION: Synthetic

<400> SEQUENCE: 7

Asn Phe Gly Ile His
1               5

<210> SEQ ID NO 8
<211> LENGTH: 16
<212> TYPE: PRT
<213> ORGANISM: Artificial Sequence
<220> FEATURE:
<223> OTHER INFORMATION: Synthetic
```

<400> SEQUENCE: 8

Val Ile Trp Gly Asp Gly Ile Thr Thr Tyr Asn Ser Val Leu Lys Ser
1               5                   10                  15

<210> SEQ ID NO 9
<211> LENGTH: 9
<212> TYPE: PRT
<213> ORGANISM: Artificial Sequence
<220> FEATURE:
<223> OTHER INFORMATION: Synthetic

<400> SEQUENCE: 9

Ser Tyr Phe Leu Gly Ala Met Val Tyr
1               5

<210> SEQ ID NO 10
<211> LENGTH: 11
<212> TYPE: PRT
<213> ORGANISM: Artificial Sequence
<220> FEATURE:
<223> OTHER INFORMATION: Synthetic

<400> SEQUENCE: 10

Lys Ala Ser Gln Ser Val Gly Thr Ala Val Ala
1               5                   10

<210> SEQ ID NO 11
<211> LENGTH: 7
<212> TYPE: PRT
<213> ORGANISM: Artificial Sequence
<220> FEATURE:
<223> OTHER INFORMATION: Synthetic

<400> SEQUENCE: 11

Ser Ala Ser Thr Arg Tyr Thr
1               5

<210> SEQ ID NO 12
<211> LENGTH: 8
<212> TYPE: PRT
<213> ORGANISM: Artificial Sequence
<220> FEATURE:
<223> OTHER INFORMATION: Synthetic

<400> SEQUENCE: 12

Gln Gln Tyr Ser Thr Ser Arg Thr
1               5

<210> SEQ ID NO 13
<211> LENGTH: 30
<212> TYPE: DNA
<213> ORGANISM: Artificial Sequence
<220> FEATURE:
<223> OTHER INFORMATION: Synthetic

<400> SEQUENCE: 13
ggctacacct tcacagacta tcacatggat                                       30

<210> SEQ ID NO 14
<211> LENGTH: 51
<212> TYPE: DNA
<213> ORGANISM: Artificial Sequence
<220> FEATURE:
<223> OTHER INFORMATION: Synthetic

<400> SEQUENCE: 14
gacatcaacc caaacaatgg cggcgccatc tacaatcaga agtttaaggg c          51

<210> SEQ ID NO 15
<211> LENGTH: 39
<212> TYPE: DNA
<213> ORGANISM: Artificial Sequence
<220> FEATURE:
<223> OTHER INFORMATION: Synthetic

<400> SEQUENCE: 15
tctcactacg attatgctgg aggagcttgg ttcgcttac                        39

<210> SEQ ID NO 16
<211> LENGTH: 50
<212> TYPE: DNA
<213> ORGANISM: Artificial Sequence
<220> FEATURE:
<223> OTHER INFORMATION: Synthetic

<400> SEQUENCE: 16
aagagctccc agagcctgct gttctccggc aaccagaaga attacctggc            50

<210> SEQ ID NO 17
<211> LENGTH: 21
<212> TYPE: DNA
<213> ORGANISM: Artificial Sequence
<220> FEATURE:
<223> OTHER INFORMATION: Synthetic

<400> SEQUENCE: 17
tgggcttcta ccagagctag c                                          21

<210> SEQ ID NO 18
<211> LENGTH: 27
<212> TYPE: DNA
<213> ORGANISM: Artificial Sequence
<220> FEATURE:
<223> OTHER INFORMATION: Synthetic

<400> SEQUENCE: 18
cagcagtact atagcttccc aagaacc                                     27

<210> SEQ ID NO 19
<211> LENGTH: 10
<212> TYPE: PRT
<213> ORGANISM: Artificial Sequence
<220> FEATURE:
<223> OTHER INFORMATION: Synthetic

<400> SEQUENCE: 19

Gly Tyr Thr Phe Thr Asp Tyr His Met Asp
1               5                   10

<210> SEQ ID NO 20
<211> LENGTH: 17
<212> TYPE: PRT
<213> ORGANISM: Artificial Sequence
<220> FEATURE:
<223> OTHER INFORMATION: Synthetic

<400> SEQUENCE: 20

Asp Ile Asn Pro Asn Asn Gly Gly Ala Ile Tyr Asn Gln Lys Phe Lys
1               5                   10                  15

Gly

<210> SEQ ID NO 21
<211> LENGTH: 13
<212> TYPE: PRT
<213> ORGANISM: Artificial Sequence
<220> FEATURE:
<223> OTHER INFORMATION: Synthetic

<400> SEQUENCE: 21

```
Ser His Tyr Asp Tyr Ala Gly Gly Ala Trp Phe Ala Tyr
1               5                   10
```

<210> SEQ ID NO 22
<211> LENGTH: 17
<212> TYPE: PRT
<213> ORGANISM: Artificial Sequence
<220> FEATURE:
<223> OTHER INFORMATION: Synthetic

<400> SEQUENCE: 22

```
Lys Ser Ser Gln Ser Leu Leu Phe Ser Gly Asn Gln Lys Asn Tyr Leu
1               5                   10                  15
Ala
```

<210> SEQ ID NO 23
<211> LENGTH: 7
<212> TYPE: PRT
<213> ORGANISM: Artificial Sequence
<220> FEATURE:
<223> OTHER INFORMATION: Synthetic

<400> SEQUENCE: 23

```
Trp Ala Ser Thr Arg Ala Ser
1               5
```

<210> SEQ ID NO 24
<211> LENGTH: 9
<212> TYPE: PRT
<213> ORGANISM: Artificial Sequence
<220> FEATURE:
<223> OTHER INFORMATION: Synthetic

<400> SEQUENCE: 24

```
Gln Gln Tyr Tyr Ser Phe Pro Arg Thr
1               5
```

<210> SEQ ID NO 25
<211> LENGTH: 696
<212> TYPE: DNA
<213> ORGANISM: Artificial Sequence
<220> FEATURE:
<223> OTHER INFORMATION: Synthetic

<400> SEQUENCE: 25

```
gccgccacca tgggttggtc atgtattatt ctgtttctgg tggctactgc taccggcgtg      60
cattcccagg tgcagctggt ccagtctggg gctgaagtga agaagcccgg cgccaccgtg     120
aagatcagct gcaaggtgtc caactttggt atacactggg tgcagcaggc tcctggcaag     180
ggcctcgagt ggatgggcgt gatatgggt gatggaatca aacctataa ttcagttctc      240 aaatcccggg tgaccatcac agctgacacc tctacagata ccgcctatat ggagctgagc     300
tccctgagat ccgaggacac agccgtgtac tattgcgccc ggtcttattt tttgggagct     360
atggtctact ggggacaggg cacactggtg accgtgagcc gggcttccac caagggccct     420
agcgtgtttc cactggcccc ctcttccaag tctacaagcg gaggaaccgc cgctctggga     480
```

```
tgtctggtga aggattactt cccagagccc gtgaccgtgt cttggaacag cggcgctctg    540
acaagcggcg tgcacacatt tcctgccgtg ctgcagtcct ctggcctgta ctccctgagc    600
tccgtggtga cagtgccatc tagctccctg ggcacacaga cctatatctg caacgtgaat    660
cacaagccaa gcaataccaa ggtggacaag aaggtg                              696
```

<210> SEQ ID NO 26
<211> LENGTH: 708
<212> TYPE: DNA
<213> ORGANISM: Artificial Sequence
<220> FEATURE:
<223> OTHER INFORMATION: Synthetic

<400> SEQUENCE: 26

```
gccgccacca tgggctggtc atgtattatt ctgtttctgg tcgcaactgc tactggggtg    60
catagcgaaa tcgtgatgac tcagtctccc ggaaccctgt ccctgtctcc aggcgagcgg   120
gccaccctgt cctgcaaggc cagtcagagt gtgggtactg ctgtagcctg gtatcagcag   180
aagccaggcc aggctcccag gctgctgatc tactcggcat ccacccggta cactggcatc   240
cccgacaggt tcagcggctc cggctctggc acagacttca ccctgacaat ctctagactg   300
gagcctgagg acttcgccgt gtactattgc aacaatata gcacttctcg acgtttggc   360 cagggcacaa agctggagat caagcggacc gtggccgctc ccagcgtgtt catctttccc   420
ccttccgaca gcagctgaa gtccggcaca gcttctgtgg tgtgcctgct gaacaacttc   480
taccccaggg aggccaaggt ccagtggaag gtggataacg ctctgcagag cggcaattcc   540
caggagtctg tgaccgagca ggacagcaag gattccacat attctctgtc tagcacctg   600 acactgtcta aggccgatta cgagaagcac aaggtgtatg cttgtgaagt cacccaccag   660
ggtctgtcat cacccgtcac taagtctttt aaccgaggcg aatgctga              708
```

<210> SEQ ID NO 27
<211> LENGTH: 134
<212> TYPE: PRT
<213> ORGANISM: Artificial Sequence
<220> FEATURE:
<223> OTHER INFORMATION: Synthetic

<400> SEQUENCE: 27

```
Ala Ala Thr Met Gly Trp Ser Cys Ile Ile Leu Phe Leu Val Ala Thr
 1               5                  10                  15

Ala Thr Gly Val His Ser Gln Val Gln Leu Val Gln Ser Gly Ala Glu
            20                  25                  30

Val Lys Lys Pro Gly Ala Thr Val Lys Ile Ser Cys Lys Val Ser Asn
        35                  40                  45

Phe Gly Ile His Trp Val Gln Gln Ala Pro Gly Lys Gly Leu Glu Trp
    50                  55                  60

Met Gly Val Ile Trp Gly Asp Gly Ile Thr Thr Tyr Asn Ser Val Leu
65                  70                  75                  80

Lys Ser Arg Val Thr Ile Thr Ala Asp Thr Ser Thr Asp Thr Ala Tyr
                85                  90                  95

Met Glu Leu Ser Ser Leu Arg Ser Glu Asp Thr Ala Val Tyr Tyr Cys
            100                 105                 110

Ala Arg Ser Tyr Phe Leu Gly Ala Met Val Tyr Trp Gly Gln Gly Thr
        115                 120                 125

Leu Val Thr Val Ser Arg
    130
```

<210> SEQ ID NO 28
<211> LENGTH: 128
<212> TYPE: PRT
<213> ORGANISM: Artificial Sequence
<220> FEATURE:
<223> OTHER INFORMATION: Synthetic

<400> SEQUENCE: 28

```
Ala Ala Thr Met Gly Trp Ser Cys Ile Ile Leu Phe Leu Val Ala Thr
1               5                   10                  15

Ala Thr Gly Val His Ser Glu Ile Val Met Thr Gln Ser Pro Gly Thr
            20                  25                  30

Leu Ser Leu Ser Pro Gly Glu Arg Ala Thr Leu Ser Cys Lys Ala Ser
        35                  40                  45

Gln Ser Val Gly Thr Ala Val Ala Trp Tyr Gln Gln Lys Pro Gly Gln
    50                  55                  60

Ala Pro Arg Leu Leu Ile Tyr Ser Ala Ser Thr Arg Tyr Thr Gly Ile
65                  70                  75                  80

Pro Asp Arg Phe Ser Gly Ser Gly Ser Gly Thr Asp Phe Thr Leu Thr
                85                  90                  95

Ile Ser Arg Leu Glu Pro Glu Asp Phe Ala Val Tyr Tyr Cys Gln Gln
            100                 105                 110

Tyr Ser Thr Ser Arg Thr Phe Gly Gln Gly Thr Lys Leu Glu Ile Lys
        115                 120                 125
```

<210> SEQ ID NO 29
<211> LENGTH: 726
<212> TYPE: DNA
<213> ORGANISM: Artificial Sequence
<220> FEATURE:
<223> OTHER INFORMATION: Synthetic

<400> SEQUENCE: 29

| | | | | |
|---|---|---|---|---|
| gccgccacca | tgggttggtc | atgtattatt | ctgtttctgg | tggctactgc | taccggcgtg | 60 |
| cattcccagg | tgcagctggt | ccagtctggg | gctgaagtga | agaagcccgg | cgccaccgtg | 120 |
| aagatcagct | gcaaggtgtc | cggctacacc | ttcacagact | atcacatgga | ttgggtgcag | 180 |
| caggctcctg | gcaagggcct | cgagtggatg | ggcgacatca | acccaaacaa | tggcggcgcc | 240 |
| atctacaatc | agaagtttaa | gggccgggtg | accatcacag | ctgacacctc | tacagatacc | 300 |
| gcctatatgg | agctgagctc | cctgagatcc | gaggacacag | ccgtgtacta | ttgcgcccgg | 360 |
| tctcactacg | attatgctgg | aggagcttgg | ttcgcttact | ggggacaggg | cacactggtg | 420 |
| accgtgagcc | gggcttccac | caagggccct | agcgtgtttc | cactggcccc | ctcttccaag | 480 |
| tctacaagcg | gaggaaccgc | cgctctggga | tgtctggtga | aggattactt | cccagagccc | 540 |
| gtgaccgtgt | cttggaacag | cggcgctctg | acaagcggcg | tgcacacatt | tcctgccgtg | 600 |
| ctgcagtcct | ctggcctgta | ctccctgagc | tccgtggtga | cagtgccatc | tagctccctg | 660 |
| ggcacacaga | cctatatctg | caacgtgaat | cacaagccaa | gcaataccaa | ggtggacaag | 720 |
| aaggtg | | | | | | 726 |

<210> SEQ ID NO 30
<211> LENGTH: 729
<212> TYPE: DNA
<213> ORGANISM: Artificial Sequence
<220> FEATURE:
<223> OTHER INFORMATION: Synthetic

<400> SEQUENCE: 30

```
gccgccacca tgggctggtc atgtattatt ctgtttctgg tcgcaactgc tactggggtg      60
catagcgaaa tcgtgatgac tcagtctccc ggaaccctgt ccctgtctcc aggcgagcgg     120
gccaccctgt cctgcaagag ctcccagagc ctgctgttct ccggcaacca gaagaattac    180
ctggcttggt atcagcagaa gccaggccag gctcccaggc tgctgatcta ctgggcttct    240
accagagcta gcggcatccc cgacaggttc agcggctccg gctctggcac agacttcacc    300
ctgacaatct ctagactgga gcctgaggac ttcgccgtgt actattgcca gcagtactat    360
agcttcccaa gaacctttgg ccagggcaca aagctggaga tcaagcggac cgtggccgct    420
cccagcgtgt tcatctttcc ccttccgac gagcagctga agtccggcac agcttctgtg     480
gtgtgcctgc tgaacaactt ctaccccagg gaggccaagg tccagtggaa ggtggataac    540
gctctgcaga gcggcaattc ccaggagtct gtgaccgagc aggacagcaa ggattccaca    600
tattctctgt ctagcaccct gacactgtct aaggccgatt acgagaagca caaggtgtat    660
gcttgtgaag tcacccacca gggtctgtca tcacccgtca ctaagtcttt taaccgaggc    720
gaatgctga                                                              729
```

<210> SEQ ID NO 31
<211> LENGTH: 144
<212> TYPE: PRT
<213> ORGANISM: Artificial Sequence
<220> FEATURE:
<223> OTHER INFORMATION: Synthetic

<400> SEQUENCE: 31

```
Ala Ala Thr Met Gly Trp Ser Cys Ile Ile Leu Phe Leu Val Ala Thr
  1               5                  10                  15

Ala Thr Gly Val His Ser Gln Val Gln Leu Val Gln Ser Gly Ala Glu
             20                  25                  30

Val Lys Lys Pro Gly Ala Thr Val Lys Ile Ser Cys Lys Val Ser Gly
         35                  40                  45

Tyr Thr Phe Thr Asp Tyr His Met Asp Trp Val Gln Gln Ala Pro Gly
     50                  55                  60

Lys Gly Leu Glu Trp Met Gly Asp Ile Asn Pro Asn Asn Gly Gly Ala
 65                  70                  75                  80

Ile Tyr Asn Gln Lys Phe Lys Gly Arg Val Thr Ile Thr Ala Asp Thr
                 85                  90                  95

Ser Thr Asp Thr Ala Tyr Met Glu Leu Ser Ser Leu Arg Ser Glu Asp
            100                 105                 110

Thr Ala Val Tyr Tyr Cys Ala Arg Ser His Tyr Asp Tyr Ala Gly Gly
        115                 120                 125

Ala Trp Phe Ala Tyr Trp Gly Gln Gly Thr Leu Val Thr Val Ser Arg
    130                 135                 140
```

<210> SEQ ID NO 32
<211> LENGTH: 135
<212> TYPE: PRT
<213> ORGANISM: Artificial Sequence
<220> FEATURE:
<223> OTHER INFORMATION: Synthetic

<400> SEQUENCE: 32

```
Ala Ala Thr Met Gly Trp Ser Cys Ile Ile Leu Phe Leu Val Ala Thr
  1               5                  10                  15

Ala Thr Gly Val His Ser Glu Ile Val Met Thr Gln Ser Pro Gly Thr
             20                  25                  30
```

Leu Ser Leu Ser Pro Gly Glu Arg Ala Thr Leu Ser Cys Lys Ser Ser
         35                  40                  45

Gln Ser Leu Leu Phe Ser Gly Asn Gln Lys Asn Tyr Leu Ala Trp Tyr
     50                  55                  60

Gln Gln Lys Pro Gly Gln Ala Pro Arg Leu Leu Ile Tyr Trp Ala Ser
 65                  70                  75                  80

Thr Arg Ala Ser Gly Ile Pro Asp Arg Phe Ser Gly Ser Gly Ser Gly
                 85                  90                  95

Thr Asp Phe Thr Leu Thr Ile Ser Arg Leu Glu Pro Glu Asp Phe Ala
            100                 105                 110

Val Tyr Tyr Cys Gln Gln Tyr Tyr Ser Phe Pro Arg Thr Phe Gly Gln
        115                 120                 125

Gly Thr Lys Leu Glu Ile Lys
    130                 135

<210> SEQ ID NO 33
<211> LENGTH: 66
<212> TYPE: DNA
<213> ORGANISM: Artificial Sequence
<220> FEATURE:
<223> OTHER INFORMATION: Synthetic

<400> SEQUENCE: 33
gccgccacca tgggttggtc atgtattatt ctgtttctgg tggctactgc taccggcgtg    60
cattcc                                                                66

<210> SEQ ID NO 34
<211> LENGTH: 336
<212> TYPE: DNA
<213> ORGANISM: Artificial Sequence
<220> FEATURE:
<223> OTHER INFORMATION: Synthetic

<400> SEQUENCE: 34
caggtgcagc tggtccagtc tggggctgaa gtgaagaagc ccggcgccac cgtgaagatc    60
agctgcaagg tgtccaactt tggtatacac tgggtgcagc aggctcctgg caagggcctc   120
gagtggatgg gcgtgatatg gggtgatgga atcacaacct ataattcagt tctcaaatcc   180
cgggtgacca tcacagctga cacctctaca gataccgcct atatggagct gagctccctg   240
agatccgagg acacagccgt gtactattgc gcccggtctt atttttttggg agctatggtc   300 tactggggac agggcacact ggtgaccgtg agccgg                              336

<210> SEQ ID NO 35
<211> LENGTH: 294
<212> TYPE: DNA
<213> ORGANISM: Artificial Sequence
<220> FEATURE:
<223> OTHER INFORMATION: Synthetic

<400> SEQUENCE: 35
gcttccacca agggccctag cgtgtttcca ctggcccccct cttccaagtc tacaagcgga    60
ggaaccgccg ctctgggatg tctggtgaag gattacttcc cagagcccgt gaccgtgtct   120
tggaacagcg gcgctctgac aagcggcgtg cacacatttc ctgccgtgct gcagtcctct   180
ggcctgtact ccctgagctc cgtggtgaca gtgccatcta gctccctggg cacacagacc   240
tatatctgca acgtgaatca caagccaagc aataccaagg tggacaagaa ggtg          294

```
<210> SEQ ID NO 36
<211> LENGTH: 66
<212> TYPE: DNA
<213> ORGANISM: Artificial Sequence
<220> FEATURE:
<223> OTHER INFORMATION: Synthetic

<400> SEQUENCE: 36
gccgccacca tgggctggtc atgtattatt ctgtttctgg tcgcaactgc tactggggtg    60
catagc                                                               66

<210> SEQ ID NO 37
<211> LENGTH: 318
<212> TYPE: DNA
<213> ORGANISM: Artificial Sequence
<220> FEATURE:
<223> OTHER INFORMATION: Synthetic

<400> SEQUENCE: 37
gaaatcgtga tgactcagtc tcccggaacc ctgtccctgt ctccaggcga gcgggccacc    60
ctgtcctgca aggccagtca gagtgtgggt actgctgtag cctggtatca gcagaagcca   120
ggccaggctc ccaggctgct gatctactcg gcatccaccc ggtacactgg catccccgac   180
aggttcagcg gctccggctc tggcacagac ttcaccctga caatctctag actggagcct   240
gaggacttcg ccgtgtacta ttgccaacaa tatagcactt ctcggacgtt tggccagggc   300
acaaagctgg agatcaag                                                 318

<210> SEQ ID NO 38
<211> LENGTH: 324
<212> TYPE: DNA
<213> ORGANISM: Artificial Sequence
<220> FEATURE:
<223> OTHER INFORMATION: Synthetic

<400> SEQUENCE: 38
cggaccgtgg ccgctcccag cgtgttcatc tttccccctt ccgacgagca gctgaagtcc    60
ggcacagctt ctgtggtgtg cctgctgaac aacttctacc ccaggaggc caaggtccag   120 tggaaggtgg ataacgctct gcagagcggc aattcccagg agtctgtgac cgagcaggac   180
agcaaggatt ccacatattc tctgtctagc accctgacac tgtctaaggc cgattacgag   240
aagcacaagg tgtatgcttg tgaagtcacc caccagggtc tgtcatcacc cgtcactaag   300
tcttttaacc gaggcgaatg ctga                                          324

<210> SEQ ID NO 39
<211> LENGTH: 366
<212> TYPE: DNA
<213> ORGANISM: Artificial Sequence
<220> FEATURE:
<223> OTHER INFORMATION: Synthetic

<400> SEQUENCE: 39
caggtgcagc tggtccagtc tggggctgaa gtgaagaagc ccggcgccac cgtgaagatc    60
agctgcaagg tgtccggcta caccttcaca gactatcaca tggattgggt gcagcaggct   120
cctggcaagg gcctcgagtg gatgggcgac atcaacccaa acaatggcgg cgccatctac   180
aatcagaagt ttaagggccg ggtgaccatc acagctgaca cctctacaga taccgcctat   240
atggagctga gctccctgag atccgaggac acagccgtgt actattgcgc ccggtctcac   300
tacgattatg ctgcaggagc ttggttcgct tactgggac agggcacact ggtgaccgtg   360
```

```
<210> SEQ ID NO 40
<211> LENGTH: 294
<212> TYPE: DNA
<213> ORGANISM: Artificial Sequence
<220> FEATURE:
<223> OTHER INFORMATION: Synthetic

<400> SEQUENCE: 40
gcttccacca agggccctag cgtgtttcca ctggcccct cttccaagtc tacaagcgga      60
ggaaccgccg ctctgggatg tctggtgaag gattacttcc cagagcccgt gaccgtgtct    120
tggaacagcg gcgctctgac aagcggcgtg cacacatttc ctgccgtgct gcagtcctct    180
ggcctgtact ccctgagctc cgtggtgaca gtgccatcta gctccctggg cacacagacc    240
tatatctgca acgtgaatca caagccaagc aataccaagg tggacaagaa ggtg          294

<210> SEQ ID NO 41
<211> LENGTH: 339
<212> TYPE: DNA
<213> ORGANISM: Artificial Sequence
<220> FEATURE:
<223> OTHER INFORMATION: Synthetic

<400> SEQUENCE: 41
gaaatcgtga tgactcagtc tcccggaacc ctgtccctgt ctccaggcga gcgggccacc     60
ctgtcctgca agagctccca gagcctgctg ttctccggca accagaagaa ttacctggct    120
tggtatcagc agaagccagg ccaggctccc aggctgctga tctactgggc ttctaccaga    180
gctagcggca tccccgacag gttcagcggc tccggctctg gcacagactt caccctgaca    240
atctctagac tggagcctga ggacttcgcc gtgtactatt gccagcagta ctatagcttc    300
ccaagaacct ttggccaggg cacaaagctg gagatcaag                           339

<210> SEQ ID NO 42
<211> LENGTH: 324
<212> TYPE: DNA
<213> ORGANISM: Artificial Sequence
<220> FEATURE:
<223> OTHER INFORMATION: Synthetic

<400> SEQUENCE: 42
cggaccgtgg ccgctcccag cgtgttcatc tttccccctt ccgacgagca gctgaagtcc     60
ggcacagctt ctgtggtgtg cctgctgaac aacttctacc caggggaggc caaggtccag    120
tggaaggtgg ataacgctct gcagagcggc aattcccagg agtctgtgac cgagcaggac    180
agcaaggatt ccacatattc tctgtctagc accctgacac tgtctaaggc cgattacgag    240
aagcacaagg tgtatgcttg tgaagtcacc caccagggtc tgtcatcacc cgtcactaag    300
tcttttaacc gaggcgaatg ctga                                           324
```

PREPARATION AND USE OF ANTI-MET-AND-RON BISPECIFIC ANTIBODY AND ANTIBODY-DRUG CONJUGATE THEREOF

CROSS REFERENCE TO RELATED APPLICATIONS

The present application claims the benefit of Chinese Patent Application No. 202010562324.X filed on Jun. 18, 2020, the contents of which are incorporated herein by reference in their entirety.

REFERENCE TO SEQUENCE LISTING

The Sequence Listing is submitted as an ASCII formatted text file via EFS-Web, with a file name of "Sequence_listing.txt", a creation date of Feb. 10, 2021, and a size of 19,239 bytes. The Sequence Listing filed via EFS-Web is part of the specification and is incorporated in its entirety by reference herein.

TECHNICAL FIELD

The present application relates to the field of biopharmaceuticals, and more specifically, to a preparation method and use of an anti-MET-and-RON bispecific antibody and an antibody-drug conjugate thereof.

BACKGROUND

Hepatocyte growth factor receptor (MET) and macrophage-stimulating protein receptor (RON) belong to a unique subfamily of receptor tyrosine kinases, and have similar structures and functions. Since MET and RON were discovered in 1987 and 1993 respectively, their roles in cancer have been studied in various model systems, including genetics, transcriptomics, proteomics, and tumor microenvironments. These studies have shown the importance of MET and RON in tumor initiation, progression, malignancy. Pathologically, increased expression of MET and/or RON is present in various types of cancer, including colorectal cancer, breast cancer, lung cancer and pancreatic cancer. The overexpression of MET and RON in primary tumors is also related to pathophysiological parameters and may be used as biomarkers to predict patient survival and chemotherapy response. At the cellular level, abnormal activation of MET and/or RON can promote invasive growth, distant metastasis, chemotherapy resistance and tumorigenicity of cancer cells. These activities are conducted through different intracellular signaling pathways, such as mitogen-activated protein kinase and phosphatidylinositol 3-kinase pathways. Based on these findings, MET and RON are considered to be key determinants in tumorigenesis. In addition, both receptors have been shown to be useful as drug targets for treatment of cancers with altered MET and/or RON expression and signaling.

Clinical use of MET and RON targeted therapies has been under in-depth research, and both small molecule kinase inhibitors (SMKIs) and therapeutic monoclonal antibodies (TMAB) against MET and RON have been developed. Several SMKIs, such as Cabozantinib and Crizotinib, have been approved by the FDA for clinical use. Because MET and RON are structurally similar, almost all SMKIs targeting MET are also specific to RON. TMABs against MET, such as ABT-700, SAIT301 and Sym015, are currently undergoing clinical trials. TMABS against RON, such as IMC41A10, ZT/f2, 6E6 and narnatumab have also been developed. Narnatumab had undergone clinical trials which were terminated due to lack of therapeutic effects. Recently, a strategy of using antibody-drug conjugates (ADCs) against MET and/or RON has been reported. MET-specific ADCs, including ABBV-399, TR1801-ADC and SHR-A1403 have recently entered clinical trials (www.clinicaltrials.gov). ADCs against RON, such as ZT/G4-monomethyl auristatin E (ZT/G4-MMAE) and PCM5B14-DCM (PCM5B14-DCM) have also been reported. Cumulative results have shown that both anti-MET and anti-RON ADCs can effectively inhibit and/or eradicate xenograft tumors mediated by different types of cancer cell lines in mouse models, and have good pharmacokinetic characteristics and controllable toxicological activities. Obviously, these findings laid a foundation for the use of anti-MET and anti-RON ADCs as a new strategy for cancer treatment.

In recent years, China has made great progress in the research and development of ADC drugs. Many scientific research units and pharmaceutical companies have actively been involved in the research and development of new anti-cancer drugs ADCs against different drug targets using specific monoclonal antibodies. The successful development of an antibody conjugated drug relies on the selection of an appropriate antigen target, so that an antibody portion of such a drug can bind specifically to the antigen target at a high activity. The new target antigen should be expressed at a high level in tumors, expressed at a low level or not expressed in normal tissues, or only expressed in specific tissue types, so that the drug can be safer and more effective. Bispecific antibodies, also known as bifunctional antibodies, are another research hotspot in tumor gene therapy in recent years. A bispecific antibody has two antigen binding sites, at which two different antigen epitopes may be respectively bound.

Based on the Knobs-into-holes (KiH) scheme of Roche's CrossMab technology, the present application further solves the problem of light chain mis-pairing. To put it simply, in this technology, first, a specific chemical "Knobs-into-holes" heterodimer binding is designed in Fc region, and meanwhile CH1 and CL in Fab region are exchanged, so that light chain mis-pairing can be reduced.

The dual targeting of RON and MET in the present application is superior to inhibiting anyone target alone. RON and MET can be used as suitable antigen targets for ADC drugs. An anti-MET-and-RON bispecific antibody constructed through the CrossMab technology will be conducive to tumor-specific targeted therapies.

SUMMARY

The present application provides a bispecific antibody comprising an anti-MET antibody fragment and an anti-RON antibody fragment. An anti-MET-and-RON bispecific antibody, which comprises an anti-MET antibody fragment and an anti-RON antibody fragment. The anti-MET antibody fragment and anti-RON antibody fragment are linked to each other through a specific chemical "knobs-into-holes" structure.

In the anti-RON antibody fragment, amino acid No. 393 in an amino acid sequence thereof is mutated from T to W; and in the anti-MET antibody fragment, amino acid No. 440 in an amino acid sequence thereof is mutated from Y to V, and meanwhile CH1 in a heavy chain variable region thereof and CL in a light chain variable region thereof are exchanged.

An amino acid sequence of the heavy chain variable region of the anti-MET antibody fragment namely PCM-C1D8 is shown in SEQ ID NO: 27, and an amino acid sequence of the light chain variable region thereof is shown in SEQ ID NO: 28. An amino acid sequence of a heavy chain variable region of the anti-RON antibody fragment namely PCM5B14 is shown in SEQ ID NO: 31, and an amino acid sequence of a light chain variable region thereof is shown in SEQ ID NO: 32. A variant sequence that has at least 95% identity with any of the amino acid sequences and retains a corresponding biological activity, or a variant sequence that retains the corresponding activity obtained by deleting, replacing and/or adding one or more amino acid residues to any one of the amino acid sequences.

An immunoglobulin heavy chain variable region comprises:
 CDRH1, which comprises an amino acid sequence of SEQ ID NO: 7;
 CDRH2, which comprises an amino acid sequence of SEQ ID NO: 8;
 CDRH3, which comprises an amino acid sequence of SEQ ID NO: 9.

An immunoglobulin light chain variable region comprises:
 CDRH1, which comprises an amino acid sequence of SEQ ID NO: 10;
 CDRH2, which comprises an amino acid sequence of SEQ ID NO: 11;
 CDRH3, which comprises an amino acid sequence of SEQ ID NO: 12.

An immunoglobulin heavy chain variable region comprises:
 CDRH1, which comprises an amino acid sequence of SEQ ID NO: 19;
 CDRH2, which comprises an amino acid sequence of SEQ ID NO: 20;
 CDRH3, which comprises an amino acid sequence of SEQ ID NO: 21;

An immunoglobulin light chain variable region comprises:
 CDRH1, which comprises an amino acid sequence of SEQ ID NO: 22;
 CDRH2, which comprises an amino acid sequence of SEQ ID NO: 23;
 CDRH3, which comprises an amino acid sequence of SEQ ID NO: 24.

Another embodiment of the present application is an antibody-binding fragment which comprises any one or more of antigen binding domains shown in SEQ ID NO: 27, SEQ ID NO: 28, SEQ ID NO: 31, or SEQ ID NO: 32.

The present application also comprises obtaining, by purifying from a prepared monoclonal antibody C1D8 or PCM-C1D8, a monoclonal antibody or a binding fragment thereof that can specifically recognize a human MET protein. First, a gene sequence of the monoclonal antibody or the binding fragment thereof is inserted into a complementarity determining region (CDR) sequence of a human or humanized motif; and CDRH1, CDRH2, and CDRH3 of the immunoglobulin heavy chain variable region in the monoclonal antibody or the binding fragment thereof are replaced separately or conservatively by a monoclonal antibody sequence selected from SEQ ID NO: 7-9, and CDRL1, CDRL2 and CDRL3 of the immunoglobulin light chain variable region in the monoclonal antibody or the binding fragment thereof are replaced separately or conservatively by a monoclonal antibody sequence selected from SEQ ID NO: 10-12. On the other hand, the monoclonal antibody or the binding fragment thereof is conjugated to a cytotoxic drug to form an antibody-drug conjugate. When the antibody in the conjugate is targeted and bound to a MET receptor on a cancer cell, the anti-MET antibody and the cytotoxic drug are together engulfed into the cell by endocytosis, thereby killing the tumor cell. In addition, the antibody or the binding fragment thereof may also be enabled to bind to a cytotoxic protein. In the future, the antibody or the binding fragment thereof may also be enabled to bind to more cytotoxic or chemotherapeutic drugs.

Another embodiment of the present application comprises obtaining, by purifying from a prepared monoclonal antibody H5B14 or PCM5B14, a monoclonal antibody or a binding fragment thereof that can specifically recognize a human RON protein. First, a gene sequence of the monoclonal antibody or the binding fragment thereof is inserted into a complementarity determining region (CDR) sequence of a human or humanized motif; and CDRH1, CDRH2, and CDRH3 of the immunoglobulin heavy chain variable region in the monoclonal antibody or the binding fragment thereof are replaced separately or conservatively by a monoclonal antibody sequence selected from SEQ ID NO: 19-21, and CDRL1, CDRL2 and CDRL3 of the immunoglobulin light chain variable region in the monoclonal antibody or the binding fragment thereof are replaced separately or conservatively by a monoclonal antibody sequence selected from SEQ ID NO: 22-24. On the other hand, the monoclonal antibody or the binding fragment thereof is conjugated to a cytotoxic drug to form an antibody-drug conjugate. When the antibody in the conjugate is targeted and bound to a RON receptor on a cancer cell, the anti-RON antibody and the cytotoxic drug are together engulfed into the cell by endocytosis, thereby killing the tumor cell. In addition, the antibody or the binding fragment thereof may also be enabled to bind to a cytotoxic protein. In the future, the antibody or the binding fragment thereof may also be enabled to bind to more cytotoxic or chemotherapeutic drugs.

In another embodiment of the present application, the anti-MET antibody fragment and the anti-RON antibody fragment in the bispecific antibody and PCMbs-MR are linked to each other by CrossMab technology. The main content is that: in the anti-RON antibody fragment, amino acid No. 393 in the amino acid sequence thereof is mutated from T to W; and in the anti-MET antibody fragment, amino acid No. 440 in the amino acid sequence thereof is mutated from Y to V, and meanwhile CH1 in the heavy chain variable region thereof and CL in the light chain variable region thereof are exchanged.

Another embodiment of the present application is a method for preparing a bispecific antibody or a binding fragment thereof capable of simultaneously targeting MET and RON receptors in host cells. The content of this method comprises: expressing an polypeptide including an immunoglobulin heavy chain variable region or (and) an polypeptide including an immunoglobulin light chain variable region of specific anti-human MET and RON receptor domains in host cells capable of expressing an polypeptide including an immunoglobulin heavy chain variable region polypeptide or (and) an polypeptide including an immunoglobulin light chain variable region polypeptide, so as to produce an antibody selected from PCMbs-MR or a binding fragment thereof and then purifying the antibody or the binding fragment. All the host cells are host cells of PCMbs-MR.

According to another embodiment of the present application, the embodiment includes a step of conjugating a cytotoxic agent or a chemotherapeutic agent to an antibody (including PCM-C1D8, PCM5B14, and PCMbs-MR) or a binding fragment thereof or combining the cytotoxic agent or the chemotherapeutic agent with a cytotoxic protein to prepare a fusion protein. On the other hand, host cells may be selected from bacteria, yeast, insects, plants, or mammalian cells.

Another embodiment of the present application is to conjugate the anti-MET-and-RON bispecific antibody or the binding fragment thereof to a cytotoxic drug to form an antibody-drug conjugate. When the antibody in the conjugate is targeted and bound to MET and/or RON receptors on a cancer cell, the anti-MET and/or RON antibody and the cytotoxic drug are engulfed into the cell by endocytosis, thereby killing the tumor cell. In addition, the antibody and the binding fragment thereof may also be enabled to bind to cytotoxic proteins. In the future, the antibody and the binding fragment thereof may also be combined with more cytotoxic or chemotherapeutic drugs. Furthermore, the tumors may be derived from brain, breast, cervix, pancreas, skin, prostate, liver, bladder, colon, head and neck, kidney, lung, non-small cell lung cancer, melanoma, mesothelioma, ovary, sarcoma, stomach, uterus, and medullary tube cell tumors.

The anti-MET-and-RON bispecific antibody PCMbs-MR and MMAE are uniformly labeled at a ratio of 1:4 and conjugated to each other through a protease-sensitive dipeptide linker to synthesize the antibody-drug conjugate (ADC), namely PCMdt-MMAE.

Another embodiment of the present application includes purifying a nucleic acid capable of expressing a specific binding anti-MET monoclonal antibody, the immunoglobulin heavy chain variable region and/or immunoglobulin light chain variable region of the antibody expressed has at least 95% homology with the monoclonal antibody PCM-C1D8. In one aspect, the immunoglobulin heavy chain variable region includes the heavy chain variable region of PCM-C1D8 or PCM5BI4: nucleic acid sequence SEQ ID NO: lencoding CDRH1; nucleic acid sequence SEQ ID NO: 2 encoding CDRH2; and nucleic acid sequence SEQ ID NO: 3 encoding CDRH3. The immunoglobulin light chain variable region includes the light chain variable region of PCM-C1D8: nucleic acid sequence SEQ ID NO: 4 encoding CDRL1; nucleic acid sequence SEQ ID NO: 5 encoding CDRL2; and nucleic acid sequence SEQ ID NO: 6 encoding CDRL3. On the other hand, the immunoglobulin heavy chain variable region or (and) the immunoglobulin light chain variable region may be further added with a nucleic acid sequence encoding a cytotoxic protein and capable of forming a fusion protein with the immunoglobulin heavy chain variable region or (and) the immunoglobulin light chain variable region.

Another embodiment of the present application includes purifying a nucleic acid capable of expressing a specific binding anti-RON monoclonal antibody, the immunoglobulin heavy chain variable region and/or immunoglobulin light chain variable region of the antibody expressed has at least 95% homology with the monoclonal antibody PCM-5B14. In one aspect, the immunoglobulin heavy chain variable region includes the heavy chain variable region of PCM-C1D8 or PCM5BI4: nucleic acid sequence SEQ ID NO: 13 encoding CDRH1; nucleic acid sequence SEQ ID NO: 14 encoding CDRH2; and nucleic acid sequence SEQ ID NO: 15 encoding CDRH3. The immunoglobulin light chain variable region includes the light chain variable region of PCM-C1D8: nucleic acid sequence SEQ ID NO: 16 encoding CDRL1; nucleic acid sequence SEQ ID NO: 17 encoding CDRL2; and nucleic acid sequence SEQ ID NO: 18 encoding CDRL3. On the other hand, the immunoglobulin heavy chain variable region or (and) the immunoglobulin light chain variable region may be further added with a nucleic acid sequence encoding a cytotoxic protein and capable of forming a fusion protein with the immunoglobulin heavy chain variable region or (and) the immunoglobulin light chain variable region.

Another embodiment of the present application includes a method for producing an immunoglobulin heavy chain variable region polypeptide or an immunoglobulin light chain variable region polypeptide. The method includes: (a) culturing host cells to enable the host cells to be capable of simultaneously express an immunoglobulin heavy chain variable region or (and) an immunoglobulin light chain variable region and a nucleic acid sequence encoding a cytotoxic protein, and enabling immunoglobulin heavy chain variable region or (and) light chain variable region and cytotoxic protein to form a fusion protein under an appropriate condition, so as to obtain a polypeptide of an immunoglobulin heavy chain variable region polypeptide or an immunoglobulin light chain variable region fused with the cytotoxic protein; and (b) purifying the polypeptide including the immunoglobulin heavy chain variable region or the immunoglobulin light chain variable region.

Another embodiment of the present application includes purifying a bispecific antibody targeting human MET and RON receptor domains. The method includes: (a) culturing host cells to enable the host cells to be capable of simultaneously express an immunoglobulin heavy chain variable region or (and) an immunoglobulin light chain variable region and a nucleic acid sequence encoding a cytotoxic protein, and enabling the two to form a fusion protein so that the host cells express a polypeptide including the immunoglobulin heavy chain variable region and the immunoglobulin light chain variable region, thereby producing an antibody or an antigen-binding fragment of the antibody; and (b) purifying the antibody or the antigen-binding fragment of the antibody.

Therapeutic effects of PCMdt-MMAE targeted delivery of MMAE in killing cancer cells in vitro and in eliminating xenograft tumors in vivo: It is proved that PCMdt-MMAE is highly effective in cancer treatment in vivo.

The bispecific antibody produced against MET and RON receptors strongly induces internalization of MET and RON: The bispecific antibody produced with anti-MET antibody PCM-C1D8 and anti-RON antibody PCM-5B14, which is named PCMbs-MR, can strongly induce endocytosis of MET and RON proteins in cancer cells.

Preparation of an antibody-drug conjugate (ADC) by conjugating bispecific antibody PCMbs-MR to a drug: Bispecific antibody PCMbs-MR is conjugated to drugs including doxorubicin, a maytansinoids derivative (DM1), monomethyl auristatin E (MMAE), and duocarmycin. The ADC product (PCMdt-MMAE) formed by conjugating PCMbs-MR to MMAE is used as a first choice for further research.

Therapeutic effects of PCMdt-MMAE in killing cancer cells in vitro and in eliminating xenograft tumors in vivo: PCMdt-MMAE is proved to be effective in killing cancer cells in vitro by using human tumor cell lines from such as breast cancer, colon cancer, lung cancer, and pancreatic cancer. Xenograft tumor models of human breast, colon, lung, and pancreatic cancer cell lines verify the highly effective anti-cancer therapeutic effect of PCMdt-MMAE in vivo.

The preparation of the anti-MET and/or anti-RON monoclonal antibody that specifically recognizes MET and/or RON domain provided in the present application provides a new pharmacological basis for the use of PCMdt-MMAE to induce the endocytosis of MET and/or RON in tumor cells to lead to targeted drug delivery.

DETAILED DESCRIPTION OF THE EMBODIMENTS

Figure 1:
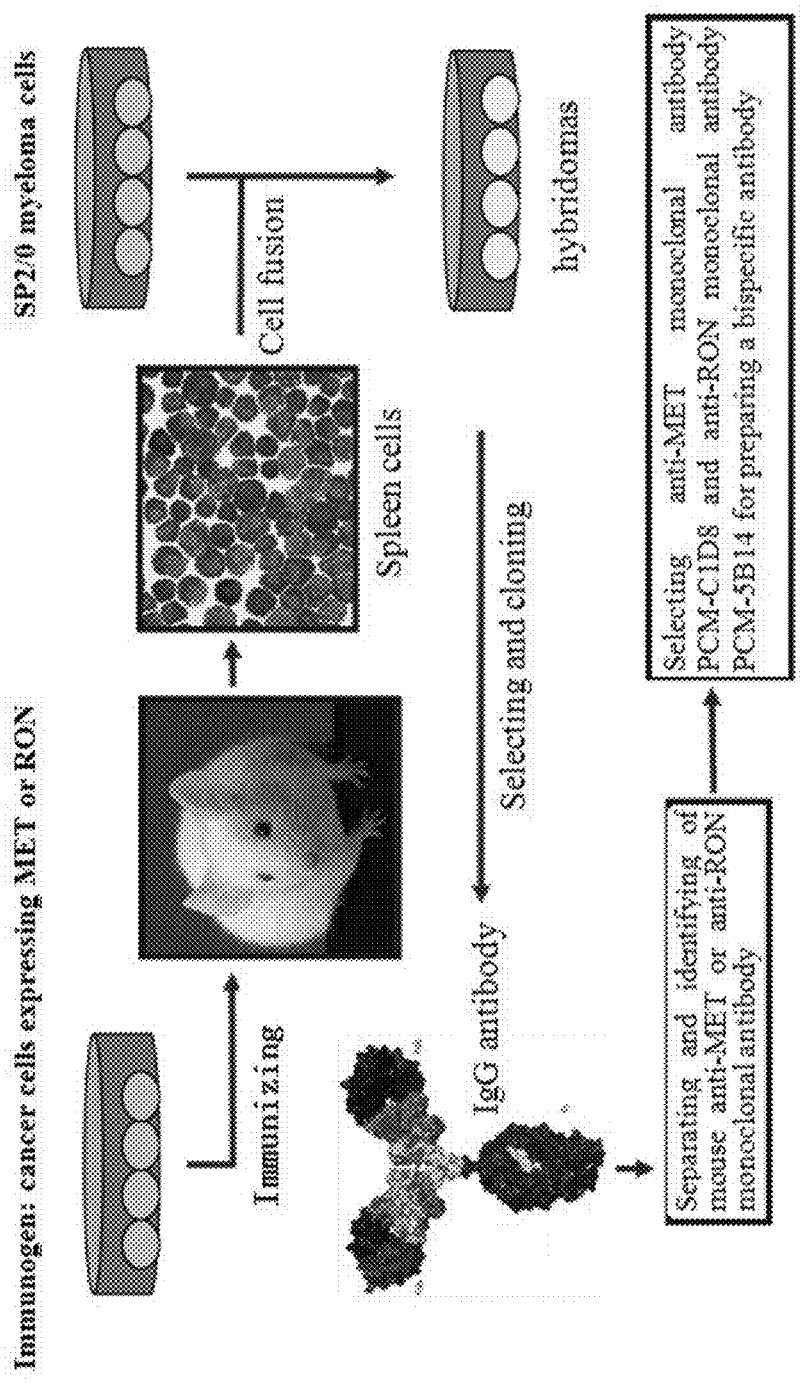
FIG. 1 schematically shows a flowchart of preparing an anti-MET monoclonal antibody and an anti-RON monoclonal antibody.

The following is a detailed description of the present application.

Although the formulation and use of various embodiments of the present application are discussed in detail below, it should be appreciated that the present application provides many embodiments that may be implemented and used in various specific environments. The specific embodiments discussed herein only illustrate specific ways of producing and using the present application, and do not limit the scope of the present application.

To facilitate the understanding of the present application, many terms are defined below. Meanings of the terms defined herein are consistent with those meanings commonly understood by those skilled in the art to which the present application pertains. Terms such as "a" and "an" are not meant to refer to only a single entity, but meant to include general categories that may be used to illustrate a specific example. The terms herein are used to describe specific embodiments, but their usage does not limit the present application except those as outlined in the claims.

The inventor of the present application has developed many bispecific antibodies targeting MET and RON receptor domains, which have shown biological effects and tumor treatment effects in preclinical models. After a bispecific antibody that recognizes MET and RON receptor domains is conjugated to a chemical drug, it can efficiently deliver a cytotoxic drug to tumor cells and kill the cancer cells in a targeted way.

The anti-MET-and-RON bispecific antibody disclosed herein are used to treat various cancers, such as non-small cell lung cancer, breast cancer, ovarian cancer, prostate cancer, cervical cancer, colorectal cancer, lung cancer, pancreatic cancer, gastric cancer, and head and neck cancer. Exposing cancer cells to an effective therapeutic dose of the antibody can inhibit or reduce proliferation of cancer cells. In some embodiments, ability of the antibody to inhibit proliferation of cancer cells can reach 40%, 50%, 60%, 70%, 80%, 90%, 95%, 98%, 99%, or 100%.

When it comes to nucleotides, terms such as the sequence referred to in the expression "substantially as SEQ ID NO: (#)", "sequence similar to . . . ", "nucleotide sequence", and similar terms refer to a sequence corresponding substantially to any part of SEQ ID NO:1 defined herein. These terms refer to synthetic and naturally-derived molecules having a sequence with a same biological, immunological, experimental or other functional activity, such as in hybridization of nucleic acid fragments, or ability to encode all or part of a RON$^{PSI}$ antibody. Of course, these terms are meant to highlight linear orders in sequences thereof.

The term "homology" refers to the degree to which two nucleic acids are complementary. Homology includes partial homology and complete homology. A partially complementary sequence is a sequence that can partially inhibit hybridization of a fully complementary sequence with a target nucleic acid, and is referred to by functional term "substantially homologous". As known to those skilled in the art, homology may be measured by hybridization or other measurement methods (for example, competitive PCR detection), and when low homology is detected, the degree of hybridization may also be measured.

An oligonucleotide sequence "substantially homologous" with an anti-MET antibody, an anti-RON antibody, and an anti-MET-and-RON bispecific antibody of SEQ ID NO: # is defined herein as a sequence that, when having more than 100 bp, exhibits greater than or equal to 75%, 80%, 85%, 90%, 91%, 92%, 93%, 94%, 95%, 96%, 97%, 98%, 99% or 100% homology with oligonucleotide sequence SEQ ID NO: #. Generally, conservative amino acid substitutions will be used to modify a sequence within the listed percentages. Conservative amino acid substitutions are well known in the art.

The term "gene" refers to a unit that encodes a functional protein, a polypeptide or an oligopeptide. As well known in the art, this functional term is meant to include at least a partial genomic sequence, a cDNA sequence or a fragment or a combination thereof, and a gene product including a gene product that may have been artificially altered. A purified gene, nucleic acid, protein, etc. is meant to refer to a product obtained after it is separated from at least one contaminating nucleic acid or protein normally associated therewith.

The term "vector" refers to a nucleic acid molecule that transfers a DNA fragment from one cell to another cell. Vectors may be further classified into vectors designed to replicate a specific sequence, or expression vectors of a promoter that may be combined with a specific sequence, or vectors designed to guide such a promoter into a nucleus. A vector may exist independent of a host cell chromosome, or may be integrated into a host cell chromosome.

The terms "host cell", "recombinant cell" or "recombinant host" refer to a cell that has been genetically engineered to contain an exogenous nucleic acid fragment or a modified fragment, whether or not it is a prokaryotic or eukaryotic cell. Therefore, a genetically engineered cell or a recombinant cell is different from a natural cell that does not contain a recombinant gene.

The term "fusion protein" refers to a hybrid protein expressed by a nucleic acid molecule containing at least two gene nucleotide sequences. For example, a fusion protein may include a polypeptide bound to an affinity matrix and another polypeptide.

The term "antibody" is meant to include polyclonal and monoclonal antibody agents, as well as hybrid antibodies, engineered antibodies, F(ab')2 fragments, F(ab) fragments, Fv fragments, single domain antibodies, chimeric antibodies, and humanized antibody agents, and functional fragments with immunological binding properties of antibody molecules.

The term "monoclonal antibody" refers to an antibody composition having a homologous population of antibodies. The term is not limited to the type or source of an antibody, nor the way it is prepared. The term is meant to include complete immunoglobulins and fragments thereof, such as Fab, F(ab')2, Fv and functional fragments with immunological binding properties of antibody molecules. In the present application, many hybridomas that have unique binding properties to a receptor domain of MET. For example, these hybridomas induce MET-specific endocytosis in MET expressing cells such as cancer cells. An example is, as used herein, hybridoma PCM-C1D8 and antibody PCM-C1D8 produced therefrom.

Methods of preparing monoclonal antibodies are known in the art. Suitable immune vectors are usually large, slow-metabolized macromolecules, such as proteins, polysaccharides, polylactic acid, polyglycolic acid, polymerized amino acids, amino acid copolymers, lipid aggregates (such as oil droplets or liposomes), and inactive virus particles. These vectors are well known to those skilled in the art. In addition, an antigen may be combined with bacterial toxins, such as toxoids from diphtheria, tetanus, cholera, etc., to enhance immunogenicity thereof.

Monoclonal antibodies are usually prepared by Kohler and Milstein's method (Nature (1975) 256:495-497) or a modified method thereof. Mice, hamsters or rats are usually immunized. Spleen and/or large lymph nodes are separated into individual cells. Then B cells and/or the separated spleen cells are induced to fuse with myeloma cells to form hybridomas (usually cells that do not express endogenous antibody heavy and/or light chains) which are then cultured in a selective medium (such as hypoxanthine, aminopterin, thymidine medium, "HAT"). Monoclonal hybridomas are obtained after limiting dilution, and the ability of the monoclonal hybridomas to produce antibodies that specifically bind to RON. Selected monoclonal antibody-secreting hybridoma cells are then cultured in vitro (for example, in a tissue culture flask or a hollow fiber reactor) or in vivo (for example, in ascites in mice).

The term "antibody fragment" refers to a part of an antibody, such as F(ab')2, F(ab)$_2$, Fab', Fab, etc. Regardless of a structure thereof, an antibody fragment can bind to a same antigen. For example, an anti-RON monoclonal antibody fragment binds to an epitope on RON.

The term "antibody fragment" refers to a synthetic or genetically engineered polypeptide capable of binding to a specific antigen, such as a polypeptide including a light chain variable region, an "Fv" fragment including a light chain variable region and a heavy chain variable region, and recombinant single chain polypeptide molecules, in which the light chain variable region and the heavy chain variable region are linked by a peptide chain linker ("scFv protein") and a smallest recognition unit including an amino acid residue that mimics a hypervariable region.

The term "chimeric antibody" refers to a recombinant protein having a variable domain and a complementarity determining region derived from a rodent antibody, while the rest part of the antibody molecule is derived from a human antibody.

The term "humanized antibody" refers to an immunoglobulin amino acid sequence variant or fragment thereof capable of binding to a predetermined antigen, and it includes an FR region and a complementarity determining region (CDR) substantially having a human immunoglobulin amino acid sequence. It substantially has a non-human immunoglobulin amino acid sequence or a sequence engineered to be capable of binding to a preselected antigen. Humanized antibodies are also commonly referred to as "mosaic" antibodies, which have a heavy chain and a light chain, or CDRs in variable regions of both a heavy chain and a light chain.

The term "antibody-drug conjugate" refers to an antibody derivative prepared by conjugating an antibody or an antibody fragment thereof, including an antibody capable of binding to a protein domain of MET and/or RON, to a cytotoxic drug, a cytostatic agent and/or a therapeutic agent. The term "therapeutic agent" refers to an agent that exerts cytotoxic, cytostatic and/or immunomodulatory effects on cancer cells or activated immune cells. Non-limiting examples of therapeutic agents include cytotoxic agents, chemotherapeutic agents, cytostatic agents, and immunomodulators. The term "chemotherapeutic agent" refers to a compound that may be used to treat cancer. The term "cytotoxic effect" refers to the depletion, elimination and/or killing of target cells using the present application. The term "cytotoxic agent" refers to an agent of the present application that has cytotoxic and cytostatic effects on target cells. The term "cytostatic effect" refers to the use of the present application to inhibit cell proliferation. The term "cytostatic agent" refers to an agent of the present application that has a cytostatic effect on cells, and can inhibit growth and/or proliferation of specific cells.

As discussed herein, a minor change in an amino acid sequence of an antibody or an immunoglobulin polypeptide is considered. For example, it is assumed that a change in an amino acid sequence maintains at least 75%, or even 80%, 90%, 95%, 96%, 97%, 98%, 99% and 100% homologous with a human framework region of a heavy chain variable domain. Specifically, in the present application, if a humanized antibody maintains at least 95%, 96%, 97%, 98%, 99% or 100% homologous with a non-CDR part of a human variable domain and a constant domain, then the humanized antibody is considered to be fully humanized.

Certain changes in amino acid sequences are considered to be conservative amino acid substitutions. Conservative substitutions are substitutions between amino acids with similar side chains. Amino acids are generally divided into the following categories: (1) non-polar: alanine, valine, leucine, isoleucine, proline, phenylalanine, methionine, tryptophan; (2) acidic: aspartic acid, glutamic acid; (3) basic: lysine, arginine, histidine; (4) polar: lysine, asparagine, glutamine, cysteine acid, serine, threonine, tyrosine. Other amino acids families include: serine and threonine which belong to an aliphatic-hydroxyl family; asparagine and glutamine which belong to an amide-containing family; alanine, valine, leucine and isoleucine which belong to a aliphatic group; phenylalanine, tryptophan and tyrosine belong to an aromatic group. Therefore, it may be reasonably contemplated that replacing leucine with isoleucine or valine alone, replacing aspartic acid with glutamic acid, replacing threonine with serine, or replacing amino acids with structurally related amino acids will not have significant influence on the binding or properties of obtained molecules, especially when the replacement does not involve amino acids in a framework region.

By measuring specific activity of a polypeptide derivative, it may be easily determined whether an amino acid change results in a functional peptide. Those skilled in the art can easily prepare a fragment or an analog of an antibody or an immunoglobulin molecule, including substitutions at amino and carboxy terminals, including preparation of a fusion protein with, for example, a cytotoxic protein. It is also possible to identify a structural domain and a functional domain by comparing nucleotide and/or amino acid sequence data (as herein shown) and/or sequence databases. Computerized comparison methods may be used to identify a sequence motif or a predicted protein conformation domain produced in other proteins of known structure and/or function. Generally, conservative amino acid substitutions do not substantially change structural features of a parental sequence (for example, a substituted amino acid should not tend to destroy a helix produced in a parental sequence, or destroy other types of auxiliary structures that characterizes a parental sequence).

The terms "cell" and "cell culture" are used interchangeably and refer to mostly, but not always, a cell in a single cell suspension or attached to a plate or tissue, including its progeny. The terms "transformants" and "transformed cells" include main subject cells and cultures derived therefrom, regardless of the number of the transformed. In addition, due to intentional or unintentional mutations, the DNA content of all progeny may not be exactly the same. The progeny includes mutant progeny having a same function or biological activity as those selected from originally transformed cells.

The terms "protein", "polypeptide" or "peptide" refer to compounds containing amino acids linked by peptide bonds and are used interchangeably.

The term "endogenous" means originating from a substance within cells. An endogenous substance is produced by metabolic activities of cells. However, an endogenous substance may be produced by manipulating cell metabolism, for example, by enabling cells to express genes encoding the substance.

The term "exogenous" means originating from a substance outside cells. However, an exogenous substance may be internalized in cells by those skilled in the art using any of a variety of known metabolic or induction methods.

The term "gene" is used to refer to a coding unit of a functional protein, a polypeptide or a peptide. As understood by those skilled in the art, this functional term includes a genomic sequence, a cDNA sequence or a fragment or a combination thereof, and a gene product, including a gene product that may have been artificially altered. Purified genes, nucleic acids, proteins, and the like, when recognized and separated from at least one contaminating nucleic acid or protein that is normally associated with them, are used to identify these entities. The term "sequence" as used herein is used to refer to nucleotides or amino acids, whether natural or artificial, such as modified nucleic acids or amino acids. When "transcribed nucleic acids" are described, 5' and 3' ends of those sequence regions located near a coding region are such that a deoxyribonucleotide sequence corresponds to a length of a full-length mRNA of a protein. The term "gene" is meant to refer to a cDNA and a genomic form of a gene. A gene can produce a variety of RNA species, which are produced by differential splicing of primary RNA transcripts. cDNAs that are spliceosomes of a same gene will include regions with an identical sequence or completely homologous (indicating presence of same exons or same exons parts on two cDNAs) and completely non-identical regions (for example, indicating presence of exon "A" on cDNA I, and cDNA 2 containing exon "B"). Because these two cDNAs include regions with identical sequences, they will be hybridized with a probe obtained from the entire gene or part of the gene containing two cDNA sequences. Therefore, the two spliceosomes are basically homologous with this probe.

The term "vector" is used to refer to a nucleic acid molecule that transfers a DNA fragment from one cell to another cell. The term "vector" as used herein is also meant to refer to an expression vector, which relates to recombinant DNA molecules containing a desired coding sequence and other appropriate nucleic acid sequences necessary for expression of the coding sequence in a specific host organism. A nucleic acid sequence necessary for expression in a prokaryote usually includes a promoter, an operon (optional), and a ribosome binding site, usually together with other sequences. It is known that eukaryotic cell can use promoters, enhancers, terminators, and polyadenylic acid signals to facilitate expression of the coding sequences.

The term "pharmaceutically acceptable" means that a component is suitable for human and/or animal use without excessive adverse side effects (such as toxicity, irritation, and allergic reactions) commensurate with a reasonable benefit/risk ratio.

The term "safe and effective amount" refers to an amount of a component sufficient to produce a desired therapeutic response without excessive adverse side effects (such as toxicity, irritation or allergic reactions) commensurate with a reasonable benefit/risk ratio at the time of use. "Therapeutically effective amount" refers to an amount of a drug of the present application effective to produce a desired therapeutic response, for example, an amount of a drug effective to delay growth of cancer or sarcoma or lymphoma or cause a cancer to shrink or not to metastasize. A specific safe and effective amount or a therapeutically effective amount will vary depending on factors such as a specific condition being treated, a patient's physical condition, a type of mammal being treated, duration of treatment, nature of complication treatment (if any), a specific formula and a structure of a compound or a derivative thereof used, etc.

The term "pharmaceutically acceptable salt" refers to an acid or a base salt used to prepare a compound. Examples of pharmaceutically acceptable salts include, but are not limited to, basic residues of mineral or organic acid salts, such as amines; and alkali or organic salts of acidic residues (such as phenols). It is preferably a salt prepared from an organic or inorganic acid. Preferred acid salts are chloride bromine, sulfate, nitrate, phosphate, sulfonate, formate, maleate, citric acid, benzoate, hydrochloride, ascorbic acid, etc. Preferred phenolic salts are alkaline earth metal salts, sodium salts, potassium salts or lithium salts.

The term "drug carrier" refers to a pharmaceutically acceptable solvent, suspension or carrier for delivering an anti-MET and/or RON antibody, and a fragment and/or an antibody-drug conjugate (ADC) thereof, or a compound, to an animal or a human body. A carrier may be a liquid or a solid which is selected according to a planned mode of administration. Proteins and liposomes are also drug carriers.

The term "cancer" refers to all types of cancer or malignancies found in humans and mammals, including cancers and sarcomas that express RON. Examples of cancers are brain cancer, breast cancer, cervical cancer, pancreatic cancer, skin cancer, prostate cancer, liver cancer, bladder cancer, colon cancer, head and neck cancer, kidney cancer, lung cancer, non-small cell lung cancer, melanoma, mesothelioma, ovarian cancer, sarcoma, gastric cancer, uterine cancer, medulloblastoma, etc.

Preparation of a monoclonal antibody that specifically recognizes MET: A MET protein was used as an immunogen to immunize a mouse. Hybridoma cells that recognized a MET receptor domain and could induce cancer cells to undergo strong MET protein endocytosis and monoclonal antibodies produced by the hybridoma cells were selected. A hybridoma named PCM-C1D8 and an antibody produced by it were selected as main candidates. FIG. 1 shows the preparation of the specific monoclonal antibody (MAB) that recognizes MET.

Humanization of PCM-C1D8: Sequences synthesized by a humanized design and including complementarity determining regions (CDRs) of five heavy chains and five light chains from PCM-C1D8 were respectively transplanted into human IgG1/k frameworks for antibody humanization to produce twenty-five different humanized IgG1/k molecules. Specificity, sensitivity, and affinity of each humanized PCM-C1D8 were analyzed. Humanized PCM-C1D8 was finally selected as the main antibody developed.

Preparation of a monoclonal antibody that specifically recognizes RON: A RON protein was used as an immunogen to immunize a mouse. Hybridoma cells that recognized a RON receptor domain and could induce cancer cells to undergo strong RON protein endocytosis and monoclonal antibodies produced by the hybridoma cells were selected. A hybridom a named PCM-5B14 and an antibody produced by it were selected as main candidates. FIG. 1 shows the preparation of the specific monoclonal antibody (MAB) that recognizes RON.

Humanization of PCM-5B14: Sequences synthesized by a humanized design and including complementarity determining regions (CDRs) of five heavy chains and five light chains from PCM-5B14 were respectively transplanted into human IgG1/k frameworks for antibody humanization to produce twenty-five different humanized IgG1/k molecules. Specificity, sensitivity, and affinity of each humanized PCM5B14 were analyzed. Humanized PCM-5B14 was finally selected as the main antibody developed.

Preparation of an anti-MET-and-RON bispecific antibody: Modifications made to prepare an anti-MET-and-anti-RON bispecific antibody mainly included: in an anti-RON antibody fragment, amino acid No. 393 in an amino acid sequence thereof was mutated from T to W; in an anti-MET antibody fragment, amino acid No. 440 in an amino acid sequence thereof was mutated from Y to V, and meanwhile CH1 in a heavy chain variable region thereof and CL in a light chain variable region thereof were interchanged. A bispecific antibody synthesized was PCMbs-MR.

Figure 3:
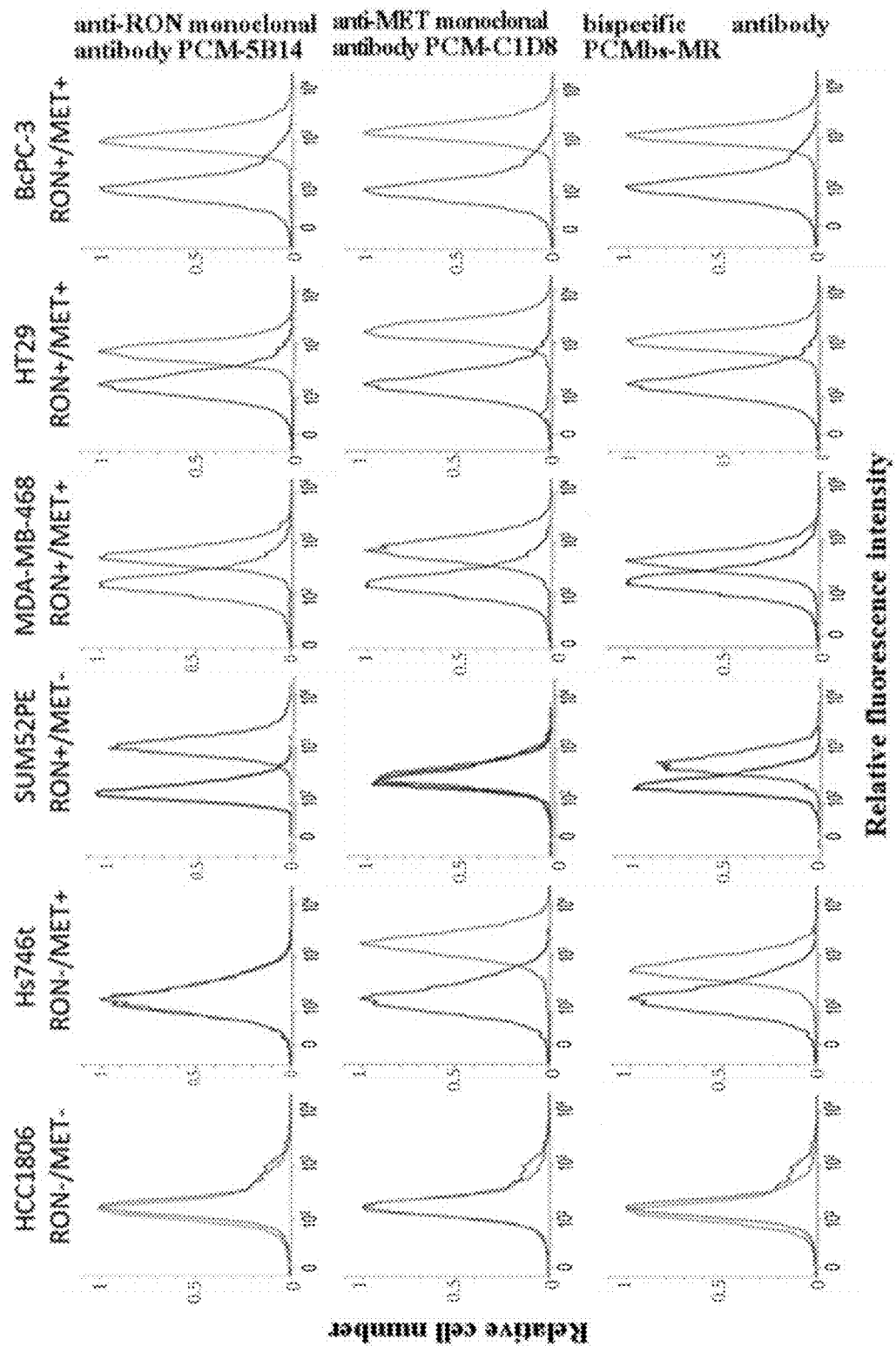
FIG. 3 shows a binding profile of anti-MET-and-anti-RON bispecific antibody PCMbs-MR to tumor cells with different expressions of MET and RON.

Experimental evidence that PCMbs-MR induces MET and/or RON endocytosis on surfaces of cancer cells: Fifteen cancer cell lines with different expression levels of MET and/or RON from human breast cancer, colon cancer, lung cancer, and pancreatic cancer and so on were used to analyze effectiveness of PCMbs-MR in inducing MET and/or RON endocytosis on surfaces of cancer cells. Representative results confirming that PCMbs-MR strongly induces MET and/or RON endocytosis are shown in FIG. 3. These results prove that PCMbs-MR is very effective in inducing RON and MET endocytosis and can deliver a sufficient amount of a cytotoxic drug for killing cancer cells.

Figure 4:
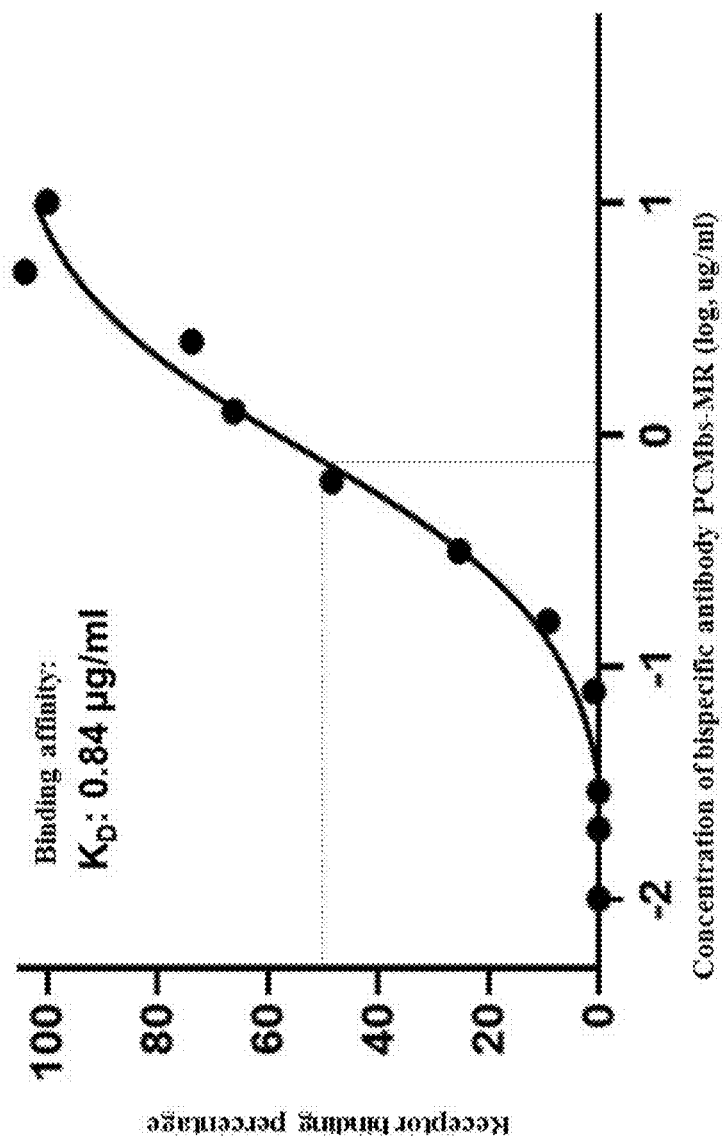
FIG. 4 shows a comprehensive affinity of anti-MET-and-anti-RON bispecific antibody PCMbs-MR in tumor cells by taking HT-29 as an example.
Figure 5:
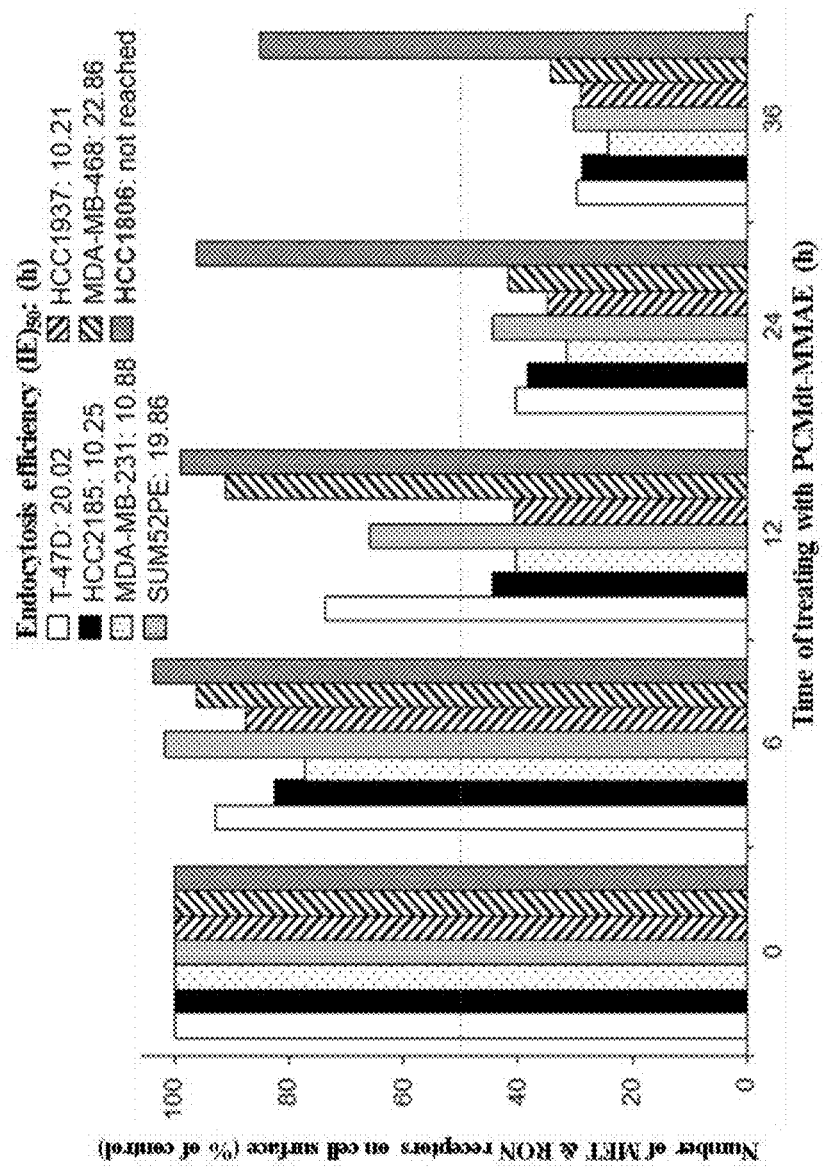
FIG. 5 shows effects of endocytosis of MET and/or RON on cell surfaces induced by bispecific antibody PCMbs-T02.

Formation of antibody-drug conjugates (ADCs) by conjugating PCMbs-MR to a plurality of cytotoxic drugs and conjugating effects thereof: Humanized PCMbs-MR was selected to be conjugated to drugs. Chemotherapeutic agents used included doxorubicin, a maytansinoids derivative (DM1), monomethyl auristatin E (MMAE), and docamicin. A product obtained by conjugating PCMbs-MR to MMAE, namely bispecific antibody PCMdt-MMAE, was finally selected as an ADC model for further research (FIG. 4). As shown in FIG. 4, PCMdt-MMAE was formed by conjugating humanized PCMbs-MR to MMAE through a protease-sensitive dipeptide linker at a drug to antibody concentration ratio (DAR) of 4:1. A conjugating proportion distribution of PCMDt and MMAE of the formed PCMdt-MMAE was analyzed by using hydrophobic interaction chromatography. Results in FIG. 5 show that antibody molecules and MMAE are distributed in a conjugating proportion of 1:4, which is in line with the proportion of antibody to drug which is 1:4.

Figure 6:
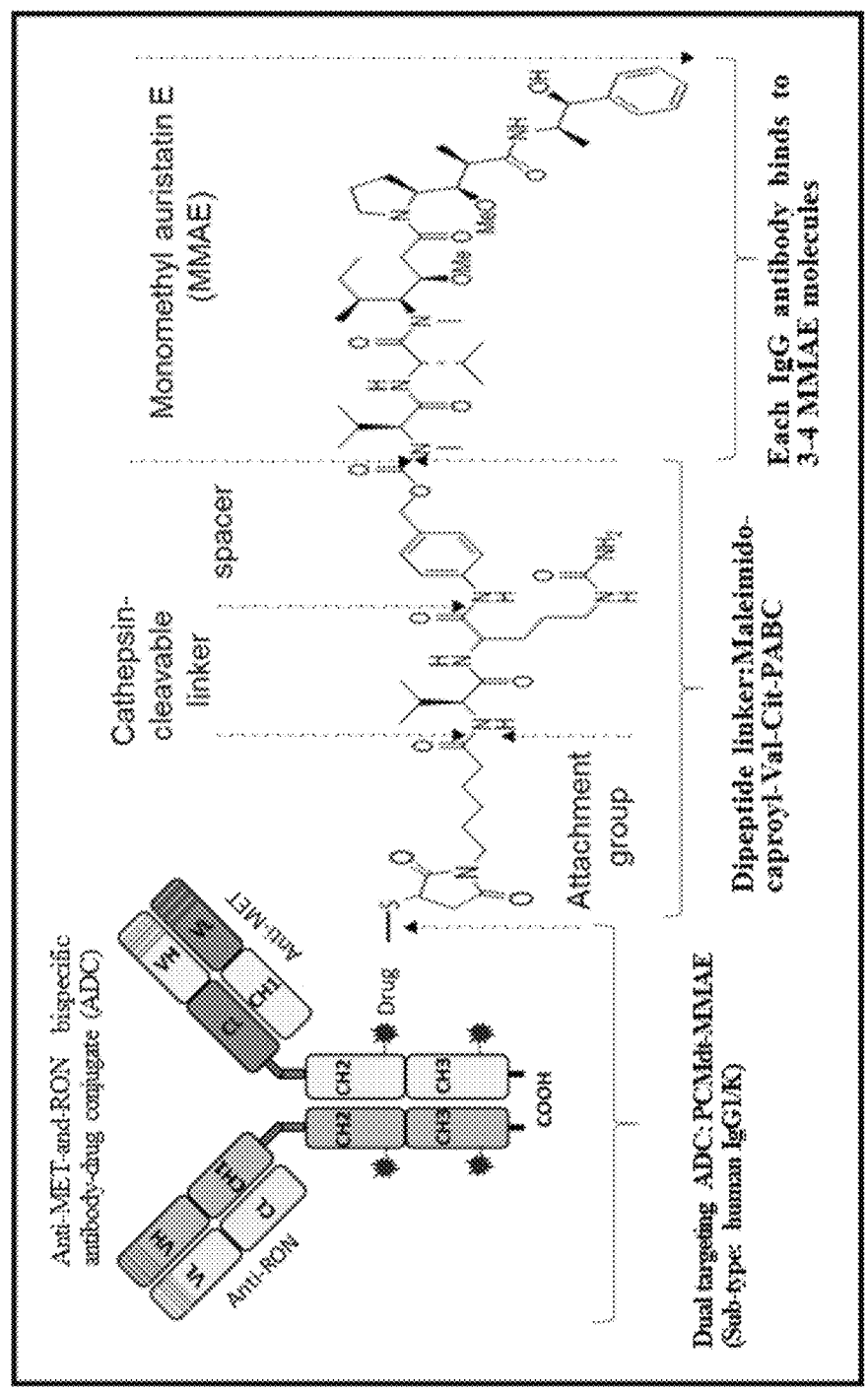
FIG. 6 shows formation of antibody-drug conjugate (ADC) PCMdt-MMAE by conjugating bispecific antibody PCMbs-T02 to a small-molecule drug MMAE.

Maximum tolerated dose of PCMdt-MMAE in animal experiments: Different doses of PCMdt-MMAE were respectively injected into mice, and changes in body weights and others of the animals were observed. Results in FIG. 6 show that a maximum tolerated dose of PCMdt-MMAE in mice is 60 mg per kilogram of body weight, which is much higher than a normal tumor treatment dose.

Figure 7:
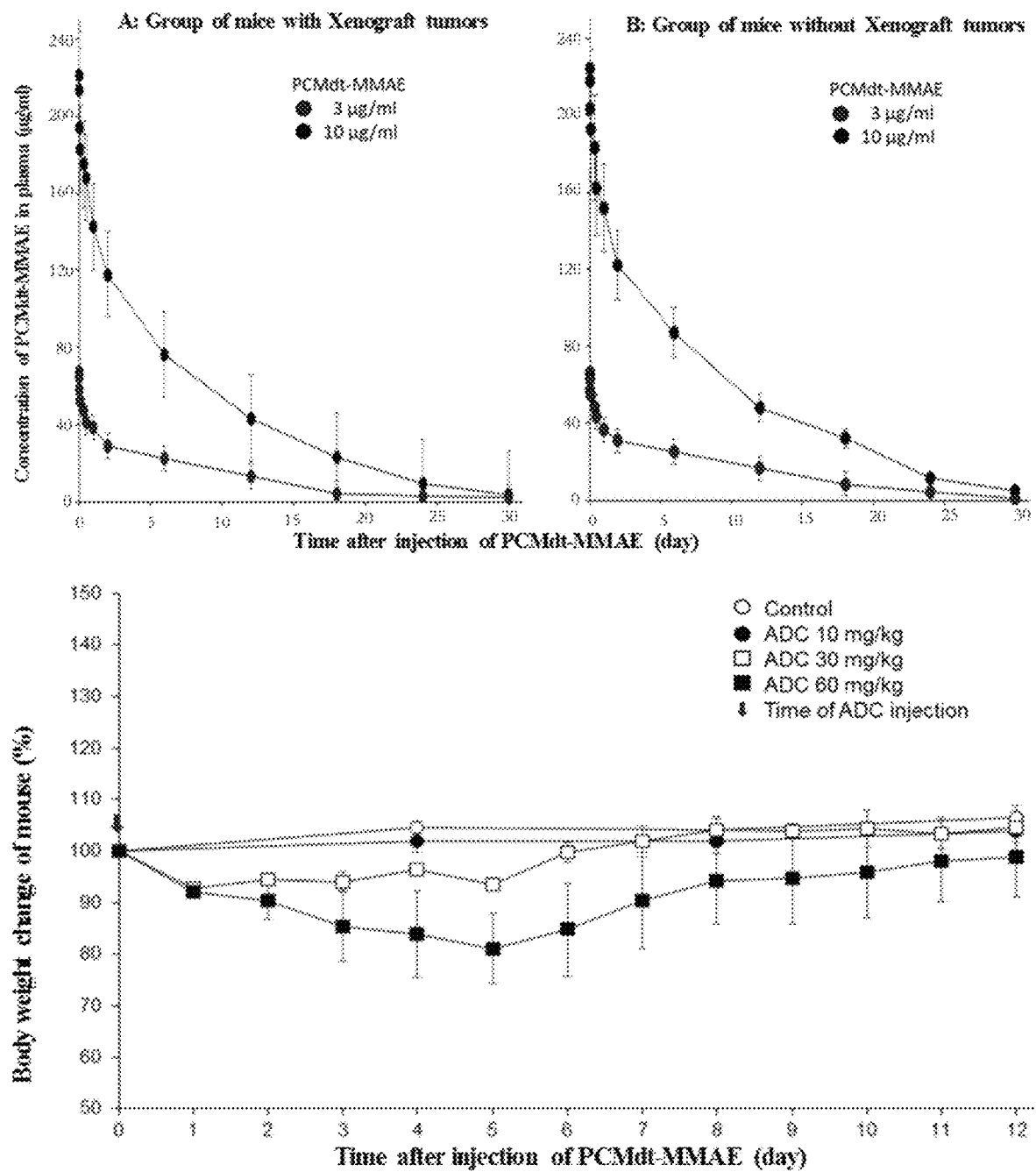
FIG. 7 shows pharmacokinetic characteristics of PCMdt-MMAE in mice with or without xenograft tumors.
Figure 8:
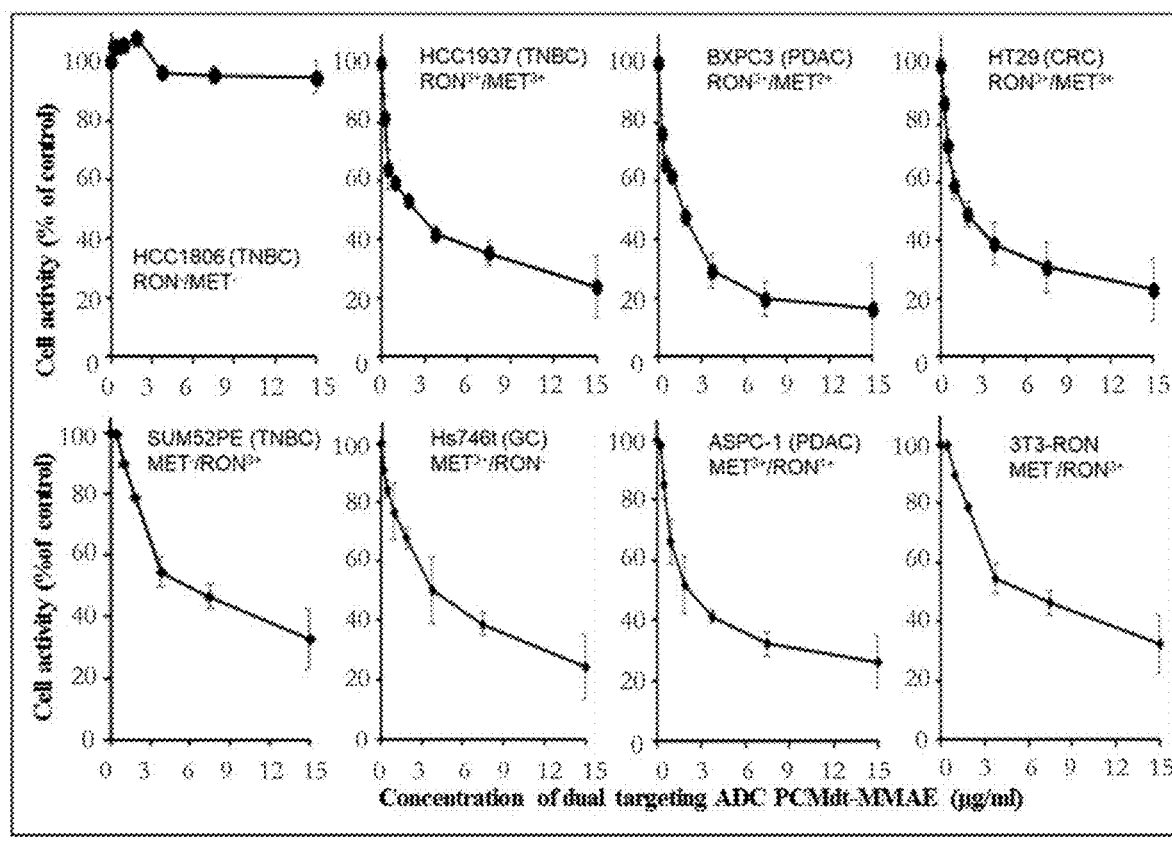
FIG. 8 shows cytotoxic effects of dual targeting antibody-drug conjugate PCMdt-MMAE on different types of human cancer cells in vitro.
Figure 9:
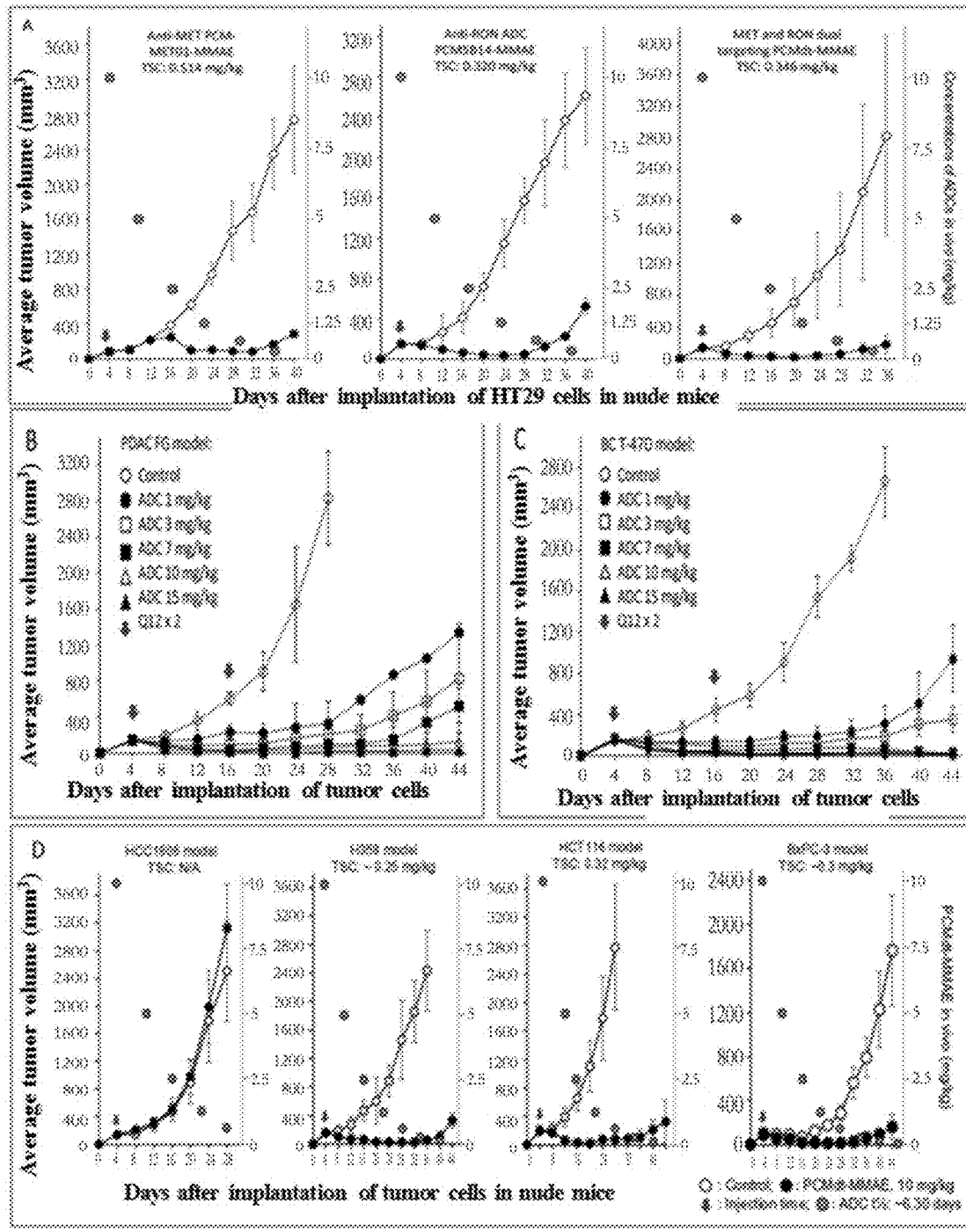
FIG. 9 shows therapeutic effects of dual targeting antibody-drug conjugate PCMdt-MMAE on mouse xenograft tumor models caused by different types of human cancer cells.

Efficacy of PCMdt-MMAE targeted delivery of MMAE in killing cancer cells in vitro and in eliminating xenograft tumors in vivo: In-vitro experiments using cell lines of multiple human cancers such as breast cancer, colon cancer, lung cancer and pancreatic cancer and so on confirmed effects of PCMdt-MMAE on killing cancer cells (FIG. 7). A median effective lethal dose is 1-3 micrograms per milliliter. In addition, xenograft tumor models of cell lines of human breast cancer, colon cancer, lung cancer, and pancreatic cancer proved a highly effective cancer treatment effect of PCMdt-MMAE in vivo (FIG. 8 and FIG. 9).

Strong induction of internalization of MET and RON by a bispecific antibody produced against MET and RON receptors: A bispecific antibody produced with anti-MET antibody PCM-C1D8 and anti-RON antibody PCM-5B14, which was named PCMbs-MR, could strongly induce endocytosis of MET and RON proteins on cancer cells.

Preparation of an antibody-drug conjugate (ADC) by conjugating the bispecific antibody PCMbs-MR to a drug: The bispecific antibody PCMbs-MR was conjugated to drugs including chemotherapeutic drugs such as doxorubicin, a maytansinoid derivatives (DM1), monomethyl auristatin E (MMAE), and docarmycin. An ADC product (PCMdt-MMAE) formed by conjugating PCMbs-MR to MMAE was taken as a first choice for further research.

Therapeutic effects of PCMdt-MMAE in killing cancer cells in vitro and in eliminating xenograft tumors in vivo: By using human tumor cell lines such as breast cancer, colon cancer, lung cancer, and pancreatic cancer and so on, it was confirmed that PCMdt-MMAE could effectively kill cancer cells in vitro. Xenograft tumor models of cell lines from human breast cancer, colon cancer, lung cancer, and pancreatic cancer verified a highly effective anti-cancer therapeutic effect of PCMdt-MMAE in vivo.

The results of the above research indicate that the production of anti-MET and/or RON monoclonal antibodies that specifically recognize MET and/or RON domains provides a new pharmacological basis for the use of PCMdt-MMAE to induce the endocytosis of MET and/or RON on tumor cells to thereby realize targeted drug delivery.

DNA sequences:
CDRs from PCM-C1D8 VH (heavy chain variable region):
CDR1:
(SEQ ID NO: 1)
AACTTTGGTATACAC (15 nt)

CDR2:
(SEQ ID NO: 2)
GTGATATGGGGTGATGGAATCACAACCTATAATTCAGTTCTCAAATCC (48 nt)

CDR3:
(SEQ ID NO: 3)
TCTTATTTTTTGGGAGCTATGGTCTAC (27 nt)

CDRs from PCM-C1D8 VL (light chain variable region):
CDR1:
(SEQ ID NO: 4)
AAGGCCAGTCAGAGTGTGGGTACTGCTGTAGCC (33 nt)

CDR2:
(SEQ ID NO: 5)
TCGGCATCCACCCGGTACACT (21 nt)

CDR3:
(SEQ ID NO: 6)
CAACAATATAGCACTTCTCGGACG (24 nt)

Amino acid sequences:
CDRs from PCM5B14 VH (heavy chain variable region):
CDR1:
(SEQ ID NO: 7)
NFGIH (5 aa)

CDR2:
(SEQ ID NO: 8)
VIWGDGITTYNSVLKS (16 aa)

CDR3:
(SEQ ID NO: 9)
SYFLGAMVY (9 aa)

CDRs from PCM5B14 VL (light chain variable region):
CDR1:
(SEQ ID NO: 10)
KASQSVGTAVA (11 aa)

CDR2:
(SEQ ID NO: 11)
SASTRYT (7 aa)

CDR3:
(SEQ ID NO: 12)
QQYSTSRT (8 aa)

DNA sequences:
CDRs from PCM5B14 VH (heavy chain variable region):
CDR1:
(SEQ ID NO: 13)
GGCTACACCTTCACAGACTATCACATGGAT (30 nt)

CDR2:
(SEQ ID NO: 14)
GACATCAACCCAAACAATGGCGGCGCCATCTACAATCAGAAGTTTAAGGGC (51 nt)

CDR3:
(SEQ ID NO: 15)
TCTCACTACGATTATGCTGGAGGAGCTTGGTTCGCTTAC (39 nt)

CDRs from PCM5B14 VL (light chain variable region):
CDR1:
(SEQ ID NO: 16)
AAGAGCTCCCAGAGCCTGCTGTTCTCCGGCAACCAGAAGAATTACCTGGCT (51 nt)

CDR2:
(SEQ ID NO: 17)
TGGGCTTCTACCAGAGCTAGC (21 nt)

CDR3:
(SEQ ID NO: 18)
CAGCAGTACTATAGCTTCCCAAGAACC (27 nt)

Amino acid sequences:
CDRs from PCM5B14 VH (heavy chain variable region):
CDR1:
(SEQ ID NO: 19)
GYTFTDYHMD (10 aa)

CDR2:
(SEQ ID NO: 20)
DINPNNGGAIYNQKFKG (17 aa)

CDR3:
(SEQ ID NO: 21)
SHYDYAGGAWFAY (13 aa)

CDRs from PCM5B14 VL (light chain variable region):
CDR1:
(SEQ ID NO: 22)
KSSQSLLFSGNQKNYLA (17 aa)

CDR2:
(SEQ ID NO: 23)
WASTRAS (7 aa)

CDR3:
(SEQ ID NO: 24)
QQYYSFPRT (9 aa)

Full-length DNA sequence of heavy chain variable region of PCM-C1D8 (SEQ ID NO: 25): Kozak—Leading peptide—VH (FR1-CDR1-FR2-CDR2-FR3-CDR3-FR4)-CHs (CH1-CH2-CH3)-Stop code Kozak:
(SEQ ID NO: 33)
GCCGCCACCATGGGTTGGTCATGTATTATTCTGTTTCTGGTGGCTACTG
CTACCGGCGTGCATTCC VH:
(SEQ ID NO: 34)
CAGGTGCAGCTGGTCCAGTCTGGGGCTGAAGTGAAGAAGCCCGGCGCCA
CCGTGAAGATCAGCTGCAAGGTGTCCAACTTTGGTATACACTGGGTGCA
GCAGGCTCCTGGCAAGGGCCTCGAGTGGATGGGCGTGATATGGGGTGAT
GGAATCACAACCTATAATTCAGTTCTCAAATCCCGGGTGACCATCACAG
CTGACACCTCTACAGATACCGCCTATATGGAGCTGAGCTCCCTGAGATC
CGAGGACACAGCCGTGTACTATTGCGCCCGGTCTTATTTTTTGGGAGCT
ATGGTCTACTGGGGACAGGGCACACTGGTGACCGTGAGCCGG
(112 aa)

CH1:
(SEQ ID NO: 35)
GCTTCCACCAAGGGCCCTAGCGTGTTTCCACTGGCCCCCTCTTCCAAGT
CTACAAGCGGAGGAACCGCCGCTCTGGGATGTCTGGTGAAGGATTACTT
CCCAGAGCCCGTGACCGTGTCTTGGAACAGCGGCGCTCTGACAAGCGGC
GTGCACACATTTCCTGCCGTGCTGCAGTCCTCTGGCCTGTACTCCCTGA
GCTCCGTGGTGACAGTGCCATCTAGCTCCCTGGGCACACAGACCTATAT

```
CTGCAACGTGAATCACAAGCCAAGCAATACCAAGGTGGACAAGAAGGTG (98 aa)
```

Full-length DNA sequence of light chain variable region of PCM-C1D8 (SEQ ID NO: 26): Kozak—leading peptide—VL (FR1-CDR1-FR2-CDR2-FR3-CDR3-FR4)—CL-Stop code

```
Kozak:
                                        (SEQ ID NO: 36)
GCCGCCACCATGGGCTGGTCATGTATTATTCTGTTTCTGGTCGCAACTG

CTACTGGGGTGCATAGC

VL:
                                        (SEQ ID NO: 37)
GAAATCGTGATGACTCAGTCTCCCGGAACCCTGTCCCTGTCTCCAGGCG

AGCGGGCCACCCTGTCCTGCAAGGCCAGTCAGAGTGTGGGTACTGCTGT

AGCCTGGTATCAGCAGAAGCCAGGCCAGGCTCCCAGGCTGCTGATCTAC

TCGGCATCCACCCGGTACACTGGCATCCCCGACAGGTTCAGCGGCTCCG

GCTCTGGCACAGACTTCACCCTGACAATCTCTAGACTGGAGCCTGAGGA

CTTCGCCGTGTACTATTGCCAACAATATAGCACTTCTCGGACGTTTGGC

CAGGGCACAAAGCTGGAGATCAAG (106 aa)

CL:
                                        (SEQ ID NO: 38)
CGGACCGTGGCCGCTCCCAGCGTGTTCATCTTTCCCCCTTCCGACGAGC

AGCTGAAGTCCGGCACAGCTTCTGTGGTGTGCCTGCTGAACAACTTCTA

CCCCAGGGAGGCCAAGGTCCAGTGGAAGGTGGATAACGCTCTGCAGAGC

GGCAATTCCCAGGAGTCTGTGACCGAGCAGGACAGCAAGGATTCCACAT

ATTCTCTGTCTAGCACCCTGACACTGTCTAAGGCCGATTACGAGAAGCA

CAAGGTGTATGCTTGTGAAGTCACCCACCAGGGTCTGTCATCACCCGTC

ACTAAGTCTTTTAACCGAGGCGAATGCTGA (107 aa)

Full-length amino acid sequence of heavy chain
variable region of PCM-C1D8:
                                        (SEQ ID NO: 27)
AATMGWSCIILFLVATATGVHSQVQLVQSGAEVKKPGATVKISCKVSNF

GIHWVQQAPGKGLEWMGVIWGDGITTYNSVLKSRVTITADTSTDTAYME

LSSLRSEDTAVYYCARSYFLGAMVYWGQGTLVTVSR

Full-length amino acid sequence of light chain
variable region of PCM-C1D8:
                                        (SEQ ID NO: 28)
AATMGWSCIILFLVATATGVHSEIVMTQSPGTLSLSPGERATLSCKASQ

SVGTAVAWYQQKPGQAPRLLIYSASTRYTGIPDRFSGSGSGTDFTLTIS

RLEPEDFAVYYCQQYSTSRTFGQGTKLEIK
```

Full-length DNA sequence of heavy chain variable region of PCM5B14 (SEQ ID NO: 29): Kozak—Leading peptide—VH (FR1-CDR1-FR2-CDR2-FR3-CDR3-FR4)-CHs (CH1-CH2-CH3)-Stop code
Kozak-Leading peptide—VH (FR1-CDR1-FR2-CDR2-FR3-CDR3-FR4)-CHs (CH1-CH2-CH3)-Stop code

```
Kozak:
                                        (SEQ ID NO: 33)
GCCGCCACCATGGGTTGGTCATGTATTATTCTGTTTCTGGTGGCTACTG

CTACCGGCGTGCATTCC

VH:
                                        (SEQ ID NO: 39)
CAGGTGCAGCTGGTCCAGTCTGGGGCTGAAGTGAAGAAGCCCGGCGCCA

CCGTGAAGATCAGCTGCAAGGTGTCCGGCTACACCTTCACAGACTATCA

CATGGATTGGGTGCAGCAGGCTCCTGGCAAGGGCCTCGAGTGGATGGGC

GACATCAACCCAAACAATGGCGGCGCCATCTACAATCAGAAGTTTAAGG

GCCGGGTGACCATCACAGCTGACACCTCTACAGATACCGCCTATATGGA

GCTGAGCTCCCTGAGATCCGAGGACACAGCCGTGTACTATTGCGCCCGG

TCTCACTACGATTATGCTGGAGGAGCTTGGTTCGCTTACTGGGGACAGG

GCACACTGGTGACCGTGAGCCGG (122 aa)

CH1:
                                        (SEQ ID NO: 40)
GCTTCCACCAAGGGCCCTAGCGTGTTTCCACTGGCCCCCTCTTCCAAGT

CTACAAGCGGAGGAACCGCCGCTCTGGGATGTCTGGTGAAGGATTACTT

CCCAGAGCCCGTGACCGTGTCTTGGAACAGCGGCGCTCTGACAAGCGGC

GTGCACACATTTCCTGCCGTGCTGCAGTCCTCTGGCCTGTACTCCCTGA

GCTCCGTGGTGACAGTGCCATCTAGCTCCCTGGGCACACAGACCTATAT

CTGCAACGTGAATCACAAGCCAAGCAATACCAAGGTGGACAAGAAGGTG (98 aa)
```

Full-length DNA sequence of light chain variable region of PCM5B14 (SEQ ID NO: 30): Kozak—leading peptide—VL (FR1-CDR1-FR2-CDR2-FR3-CDR3-FR4)—CL Stop code

```
Kozak:
                                        (SEQ ID NO: 36)
GCCGCCACCATGGGCTGGTCATGTATTATTCTGTTTCTGGTCGCAACTG

CTACTGGGGTGCATAGC

VL:
                                        (SEQ ID NO: 41)
GAAATCGTGATGACTCAGTCTCCCGGAACCCTGTCCCTGTCTCCAGGCG

AGCGGGCCACCCTGTCCTGCAAGAGCTCCCAGAGCCTGCTGTTCTCCGG

CAACCAGAAGAATTACCTGGCTTGGTATCAGCAGAAGCCAGGCCAGGCT

CCCAGGCTGCTGATCTACTGGGCTTCTACCAGAGCTAGCGGCATCCCCG

ACAGGTTCAGCGGCTCCGGCTCTGGCACAGACTTCACCCTGACAATCTC

TAGACTGGAGCCTGAGGACTTCGCCGTGTACTATTGCCAGCAGTACTAT

AGCTTCCCAAGAACCTTTGGCCAGGGCACAAAGCTGGAGATCAAG

CL:
                                        (SEQ ID NO: 42)
CGGACCGTGGCCGCTCCCAGCGTGTTCATCTTTCCCCCTTCCGACGAGC

AGCTGAAGTCCGGCACAGCTTCTGTGGTGTGCCTGCTGAACAACTTCTA

CCCCAGGGAGGCCAAGGTCCAGTGGAAGGTGGATAACGCTCTGCAGAGC

GGCAATTCCCAGGAGTCTGTGACCGAGCAGGACAGCAAGGATTCCACAT

ATTCTCTGTCTAGCACCCTGACACTGTCTAAGGCCGATTACGAGAAGCA

CAAGGTGTATGCTTGTGAAGTCACCCACCAGGGTCTGTCATCACCCGTC

ACTAAGTCTTTTAACCGAGGCGAATGCTGA (107 aa)
```

-continued

Full-length amino acid sequence of heavy chain
variable region of PCM5B14:
(SEQ ID NO: 31)
AATMGWSCIILFLVATATGVHSQVQLVQSGAEVKKPGATVKISCKVSGY

TFTDYHMDWVQQAPGKGLEWMGDINPNNGGAIYNQKFKGRVTITADTST

DTAYMELSSLRSEDTAVYYCARSHYDYAGGAWFAYWGQGTLVTVSR

Full-length amino acid sequence of light chain
variable region of PCM5B14:
(SEQ ID NO: 32)
AATMGWSCIILFLVATATGVHSEIVMTQSPGTLSLSPGERATLSCKSSQ

SLLFSGNQKNYLAWYQQKPGQAPRLLIYWASTRASGIPDRFSGSGSGTD

FTLTISRLEPEDFAVYYCQQYYSFPRTFGQGTKLEIK

FIG. 1 schematically shows a flowchart of preparing an anti-MET monoclonal antibody and an anti-RON monoclonal antibody as well as the antibodies. A MET protein or a RON protein was used as an immunogen to immunize a mouse. Spleen cells of the immunized mouse were taken to fuse with mouse myeloma cells SP2/0. Hybridoma cells that recognized a MET or RON receptor domain and could induce cancer cells to undergo strong endocytosis of MET or RON protein as well as a monoclonal antibody produced by the hybridoma cells were selected. Then CDRs of a heavy chain variable region and a light chain variable region in a structure of the antibody were retained. Antibody frameworks of the antibody were substituted with a humanized sequence. An anti-MET humanized antibody and an anti-RON humanized antibody were named PCM-C1D8 and PCM-5B14, respectively.

Figure 2:
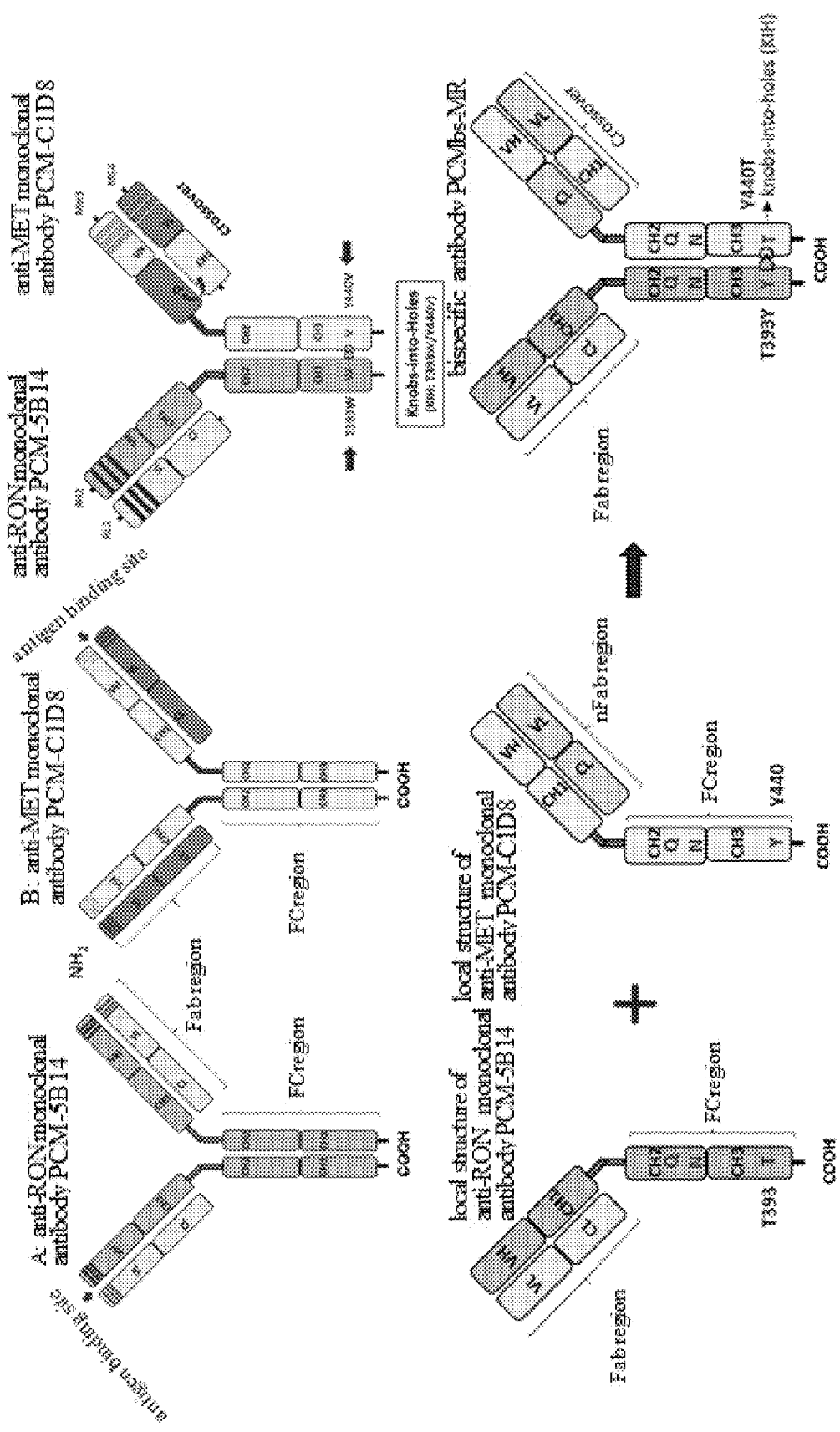
FIG. 2 schematically shows humanized anti-RON monoclonal antibody PCM5B14 and humanized anti-MET monoclonal antibody PCM-C1D8 as well as a flowchart of assembling PCM5B14 and PCM-C1D8 into an anti-MET-and-RON bispecific antibody.

FIG. 2 schematically shows humanized anti-RON monoclonal antibody PCM5B14 and humanized anti-MET monoclonal antibody PCM-C1D8 as well as a flowchart of assembling PCM5B14 and PCM-C1D8 into anti-MET-and-RON bispecific antibody PCMbs-MR. Modifications made to prepare anti-MET-and-anti-RON bispecific antibody PCMbs-MR mainly included the following: in an anti-RON antibody fragment, amino acid No. 393 in an amino acid sequence thereof was enabled to mutate from T to W; and in an anti-MET antibody fragment, amino acid No. 440 in an amino acid sequence thereof was enabled to mutate from Y to V, and meanwhile CH1 in a heavy chain variable region thereof and CL in a light chain variable region thereof were interchanged. A synthesized bispecific antibody was PCMbs-MR.

FIG. 3 shows a binding profile of anti-MET-and-anti-RON bispecific antibody PCMbs-MR to tumor cells with different expressions of MET and RON. PCMbs-MR can interact with MET and RON on surfaces of tumor cells positive for MET and/or RON.

As shown in FIG. 4, by using colon cancer HT29 cell line positive for both MET and RON as a test model, it was found that a comprehensive affinity $K_d$ of bispecific antibody PCMbs-MR with these two receptors was 0.84 µg/ml.

As shown in FIG. 5, effects of endocytosis of MET and/or RON on cell surfaces induced by PCMbs-MR were tested. Cell lines T47-D, HCC1937, HCC2185, MDA-MB-486, MDA-MB-231, SUM52PE, and HCC1806 with different expressions of MET and/or RON were tested. Among them, HCC1806 which was negative for both MET and RON was used as a negative control. Time required for PCMbs-MR to induce endocytosis of 50% receptors on the cell surfaces (IE50) was 10.25-22.86 hours. The cells were incubated together with 5 ug/ml PCMbs-MR for different periods of time. After the antibody bound on the cell surfaces was removed by an acid buffer, RON molecules remaining on the cell surfaces were detected by using FITC-labeled goat anti-mouse IgG1 antibody and the anti-MET and anti-RON antibodies. A BD flow cytometer was used to analyze immunofluorescence intensity from each sample. A minimum period of time (hours) required to reduce RON on the cell surfaces by 50% was defined as $EC_{50}$.

FIG. 6 shows synthesizing of an antibody-drug conjugate (ADC) namely PCMdt-MMAE by conjugating anti-MET-and-RON bispecific antibody PCMbs-MR to MMAE, labeled uniformly at a ratio of 1:4, through a protease-sensitive dipeptide linker. MMAE is a highly effective tubulin inhibitor that can block cell mitosis and cause cell death.

FIG. 7 shows toxicological effects of the antibody-drug conjugate on body weights and survival of mice, i.e., an analysis of pharmacokinetic characteristics and toxic activity of PCMdt-MMAE in mice. Female Balb/c mice with or without BxPC-3 tumor cell-mediated xenograft tumors were used as models. All mice were injected with 10 mg/kg PCMdt-MMAE via tail vein. Body weights of individual mice were measured to obtain an average body weight of each group of mice. Body weights of the mice (18-20 g/mouse) before the injection were set to 100%. Daily activities, body weights, and death of the mice were monitored daily. A MMAE-ADC enzyme-linked immunoreaction (ELISA) kit was used to measure a content of MMAE-conjugated PCMbs-MR in plasma. Results of the studies show that PCMdt-MMAE at a therapeutic dose was not toxic to the tested mice. In addition, the tested mice had a good tolerance to 60 mg/kg H5B14-MMAE.

FIG. 8 shows cytotoxic effects of PCMdt-MMAE on different types of human cancer cell lines in vitro. These different types of human cancer cell lines included eight cell lines from human cancers which were colon cancer, breast cancer, pancreatic cancer, etc. A cancer cell line that did not express RON was used as a control. At the same time, PCMdt-MMAE was compared with a mouse-derived anti-MET ADC namely PCM-C1D8-MMAE and an anti-RON ADC namely Zt/g4-MMAE. Cancer cells were treated with different doses of PCMdt-MMAE for 72 hours, and cell survival rates were measured by a standard MTS method. Results of these studies indicate that PCMdt-MMAE is highly specific to cancer cells expressing MET and/or RON, and a minimum amount of PCMdt-MMAE required to kill 50% of cancer cells (IC50) is between 1 ug/ml and 4 ug/ml, depending on different cancer cell lines.

FIG. 9 shows therapeutic effects of PCMdt-MMAE on four mouse xenograft models in vivo. Six-week-old female athymic nude mice each were injected subcutaneously with $5 \times 10^6$ cells from a respective one of cell lines. The cancer cell lines used were HCC1806, HT29, FG, T-47D, HCT116, BxPC-3, and H358. The mice were randomly divided into different groups (five mice in each group). Treatment was started when all tumors reached an average tumor volume of ~150 mm³. Different doses of PCMdt-MMAE, PCM-C1D8-MMAE, or PCM5B14-MMAE were injected into the mice through tail vein. A dose-dependent study was performed in mice by injecting variable amounts of PCMdt-MMAE on a Q12×2 schedule. Tumor volumes were measured every four days. Results of these studies prove the effectiveness of PCMdt-MMAE in suppressing xenograft tumors. PCMdt-MMAE reduced tumor volumes by up to 93% on average. Second, the anti-cancer activity of PCMdt-MMAE is dose-dependent. 1 mg/kg PCMdt-MMAE is sufficient to inhibit tumor growth and prevent tumor regrowth for up to two weeks. An increase of PCMdt-MMAE by up to 7, 10, and 15 mg/kg can significantly inhibit tumor growth and result in a higher therapeutic index. Third, PCMdt-MMAE can inhibit growth of tumors mediated by cancer cells from multiple sources, including cancer cells from colon, lung, pancreas and breast, regardless of metastasis and chemoresistance status thereof. This indicates that PCMdt-MMAE has a wide range of anti-cancer activities and is suitable for treatment of various types of cancer. Finally, effects of PCMdt-MMAE are long-lasting. When injected at a single dose of 10 mg/kg, PCMdt-MMAE can inhibit growth of xenograft tumors for nearly four weeks.

It can be expected that any of the embodiments discussed in this specification may be implemented by any method, kit, and reagent of the present application, or combinations thereof, and vice versa.

It must be clearly noted that the specific embodiments described herein are illustrated by examples rather than by ways of limiting the present application. Main features of the present application may be used in various embodiments without departing from the scope of the present application. Those skilled in the art will find out, or be able to determine merely by means of routine experimentation, many equivalents to the specific steps described herein. Such equivalents are considered to be within the scope of the present application and are covered by the claims.

All publications and patent applications mentioned in this specification reflect the current technical status of the field to which the present application pertains. All these publications and patent applications are incorporated herein by reference, to an extent the same as a degree of relevance of each independent publication or patent application to the present application.

The word "a" or "an", when used in conjunction with the terms "comprise", "include", or any varied forms thereof, in the claims and/or specification, can mean "one" but also has a meaning the same as "one or more", "at least one", "one or more than one". The term "or" used in the claims means "and/or", unless it is clearly indicated that it only means an alternative or that alternatives are mutually exclusive, although the disclosed contents support the meanings of it meaning only an alternative and "and/or". The term "approximately" throughout this disclosure is used to describe a value that includes an inherent variation in errors of a device and a method used to determine the value, or a variation that exists between subjects in a study.

As used in this specification and claims, the words "contain" (and any form of "contain"), "have" (and any form of "have"), "include" (and any form of "include") or "comprise" (and any form of "comprise") are inclusive or open-ended, and do not exclude additional, unmentioned elements or method steps. As used herein, the phrase "substantially consists of . . . " limits a scope of a claim to specified substances or steps as well as those basic and novel features that do not materially affect the claimed subject matter. As used herein, the phrase "consists of . . . " does not include any of elements, steps, or ingredients not specified in a claim, except, for example, interference generally related to the elements or limitation.

The term "or a combination thereof" used herein refers to all permutations and combinations of items listed before the term. For example, "A, B, C, or a combination thereof" is meant to include at least one of A, B, C, AB, AC, BC, or ABC, and if order is important in a particular context, it is also meant to include BA, CA, CB, CBA, BCA, ACB, BAC or CAB. Continuing this example, it is obvious that it is meant to include combinations of repeated one or more items or terms, such as BB, AAA, AB, BBC, AAABCC CC, CBBAAA, CABABB, etc. Those skilled in the art will appreciate that there is generally no limit to the number of items or terms in any combination, unless it is obviously indicated from the context.

As used herein, words expressing approximation such as but not limited to "about", "essential" or "substantially" refer to such a situation where when such a modification is used it is interpreted to not necessarily be absolute or precise, but be considered to be close enough to a situation considered to be usable by those skilled in the art as the current situation. The extent to which the specification may be changed depends on an extent of a change made which allows those skilled in the art to believe that a changed feature still has a required property and an ability of an unaltered feature. In general, consistent with the previous discussion, a value modified by an approximate word such as "about" can vary from an asserted value by at least ±1%, 2%, 3%, 4%, 5%, 6%, 7%, 10%, 12% or 15%.

According to the disclosure of the present application, all the compositions and/or methods disclosed and claimed herein may be prepared and implemented through appropriate experiments. Although the compositions and methods of the present application have been described in terms of preferred embodiments, it is obvious to those skilled in the art that without departing from the concept, spirit and scope of the present application, the compositions and/or methods as well as steps of the methods or orders of the steps of the methods described herein may be changed. All such similar substitutions and modifications obvious to those skilled in the art are considered to be within the spirit, scope and concept of the present application defined by the appended claims.

What is claimed is:

1. An anti-MET-and-RON bispecific antibody, comprising an anti-MET antibody fragment and an anti-RON antibody fragment which are linked to each other through a chemical "knobs-into-holes" structure, wherein in the anti-RON antibody fragment, amino acid No. 393 in an amino acid sequence thereof is mutated from T to W, and in the anti-MET antibody fragment, amino acid No. 440 in an amino acid sequence thereof is mutated from Y to V, meanwhile CH1 in a heavy chain variable region thereof and CL in a light chain variable region thereof are interchanged; wherein the bispecific antibody comprises a domain that specifically recognizes and binds to an antigen MET on a cell surface, wherein the domain comprises a heavy chain variable region and a light chain variable region of an anti-MET specific antibody, the heavy chain variable region comprising the amino acid sequence of SEQ ID NO: 27, and the light chain variable region comprising the amino acid sequence of SEQ ID NO: 28;

wherein
the heavy chain variable region comprises:
CDRH1, which comprises the amino acid sequence of SEQ ID NO: 7;
CDRH2, which comprises the amino acid sequence of SEQ ID NO: 8; and
CDRH3, which comprises the amino acid sequence of SEQ ID NO: 9;
the light chain variable region comprises:
CDRL1, which comprises the amino acid sequence of SEQ ID NO: 10;
CDRL2, which comprises the amino acid sequence of SEQ ID NO: 11; and
CDRL3, which comprises the amino acid sequence of SEQ ID NO: 12.

2. The bispecific antibody according to claim 1, further comprising a domain that specifically recognizes and binds an antigen RON on a cell surface, wherein the domain comprises a heavy chain variable region and light chain variable region of an anti-RON specific antibody, the heavy chain variable region comprising the amino acid sequence of SEQ ID NO: 31, and the light chain variable region comprising the amino acid sequence of SEQ ID NO: 32;
wherein
the heavy chain variable region comprises:
CDRH1, which comprises the amino acid sequence of SEQ ID NO: 19;
CDRH2, which comprises the amino acid sequence of SEQ ID NO: 20; and
CDRH3, which comprises the amino acid sequence of SEQ ID NO: 21;
the light chain variable region comprises:
CDRL1, which comprises the amino acid sequence of SEQ ID NO: 22;
CDRL2, which comprises the amino acid sequence of SEQ ID NO: 23; and
CDRL3, which comprises the amino acid sequence of SEQ ID NO: 24.

3. An antibody binding fragment, comprising antigen binding domains in SEQ ID NO: 27 and SEQ ID NO: 28.

4. An anticancer drug comprising the bispecific antibody of claim 1.

5. An anticancer drug comprising the antibody binding fragment of claim 3.

6. An antibody-drug conjugate, comprising the bispecific antibody of claim 1 conjugated to a chemotherapeutic drug, or a fusion protein formed by fusing the bispecific antibody with a cytotoxic protein, wherein the antibody-drug conjugate enables the antibody to be targeted and bound to a MET and/or RON protein on a surface of a target cell, and enables the anti-MET-and-RON bispecific antibody and the drug to be engulfed together into the target cell by endocytosis.

7. An anticancer drug comprising the antibody-drug conjugate of claim 6.

8. An anti-MET specific antibody, comprising a domain that specifically recognizes and binds to an antigen MET on a cell surface, wherein the domain comprises a heavy chain variable region and a light chain variable region of the anti-MET specific antibody, the heavy chain variable region comprising the amino acid sequence of SEQ ID NO: 27, and the light chain variable region comprising the amino acid sequence of SEQ ID NO: 28.

9. An antibody-drug conjugate, comprising the anti-MET specific antibody of claim 8 conjugated to a chemotherapeutic drug, or a fusion protein formed by fusing the antibody with a cytotoxic protein, wherein the antibody-drug conjugate enables the antibody to be targeted and bound to a MET protein on a surface of a cancer cell, and enables the anti-MET specific antibody and the drug be engulfed together into the cancer cell by endocytosis, to effectively inhibit or reduce proliferation of the cancer cell.

10. An anticancer drug comprising the antibody-drug conjugate of claim 9.

11. The antibody binding fragment of claim 3, further comprising antigen binding domains in SEQ ID NO: 31 and SEQ ID NO: 32.

* * * * *